(12) United States Patent
Gallagher et al.

(10) Patent No.: US 8,354,125 B2
(45) Date of Patent: Jan. 15, 2013

(54) EX-VIVO TREATMENT OF PERIPHERAL BLOOD LEUKOCYTES WITH IFN-λ

(76) Inventors: Grant Gallagher, Milltown, NJ (US); Joyce Eskdale, Milltown, NJ (US); Shekar Srinivas, Princeton Junction, NJ (US); Jihong Dai, Ambler, PA (US); Nicholas Megjugorac, Lopatcong, NJ (US); Grant E. Gallagher, Milltown, NJ (US)

( * ) Notice: Subject to any disclaimer, the term of this patent is extended or adjusted under 35 U.S.C. 154(b) by 132 days.

(21) Appl. No.: 12/290,052

(22) Filed: Oct. 27, 2008

(65) Prior Publication Data

US 2012/0058081 A1 Mar. 8, 2012

Related U.S. Application Data

(60) Provisional application No. 60/983,168, filed on Oct. 27, 2007.

(51) Int. Cl.
*A61K 35/14* (2006.01)
*A61K 38/21* (2006.01)

(52) U.S. Cl. ........................................ 424/534; 424/85.5
(58) Field of Classification Search .................. None
See application file for complete search history.

(56) References Cited

U.S. PATENT DOCUMENTS

| 7,351,689 B2 | 4/2008 | Doyle et al. |
| 7,588,918 B2 | 9/2009 | Brady et al. |
| 2009/0220511 A1 | 9/2009 | Kotenko et al. |

FOREIGN PATENT DOCUMENTS

| WO | WO03/066002 | 8/2003 |
| WO | WO2007/029041 | 3/2007 |

OTHER PUBLICATIONS

Shapiro et al., Blood, 84: 3567-3574, 1994.*
Wills-Karp et al., Curr. Opinion in Pulmonary Med. 9: 21-27, 2003.*
Jordan et al., Gene and Immunity 8: 254-261, 2007.*
Kreijveld et al., J. Immunological Methods 314: 103-113, 2006.*
Ausubel et al., Current Protocols in Molecular Biology, John Wiley & Sons, New York, NY, 1998.
Sambrook et al., Molecular Cloning: A Laboratory Manual, 2nd ed., Cold Spring Harbor Laboratory Press, Plainview, NY, 1989.
Kaufman et al., eds., Handbook of Molecular and Cellular Methods in Biology and Medicine, CRC Press, Boca Raton, FL, 1995.
Remington's Pharmaceutical Sciences, 18th ed., Mack Publishing Co., Easton, PA, 1990.

* cited by examiner

*Primary Examiner* — Gyan Chandra
(74) *Attorney, Agent, or Firm* — Siu K. Lu

(57) ABSTRACT

The present invention provides a method of treating Th2-associated diseases and disorders by modulating the expression or secretion of IL-4, IL-5 and IL-13 using interferon lambda (IFN-λ). For Th2-associated diseases and disorders, cells of a patient having a Th2-associated disease or disorder are treated ex vivo, with IFN-λ and returned to the patient. The present invention also provides a method of ex vivo treatment, in conjunction with co-administration of IFN-λ.

14 Claims, 19 Drawing Sheets

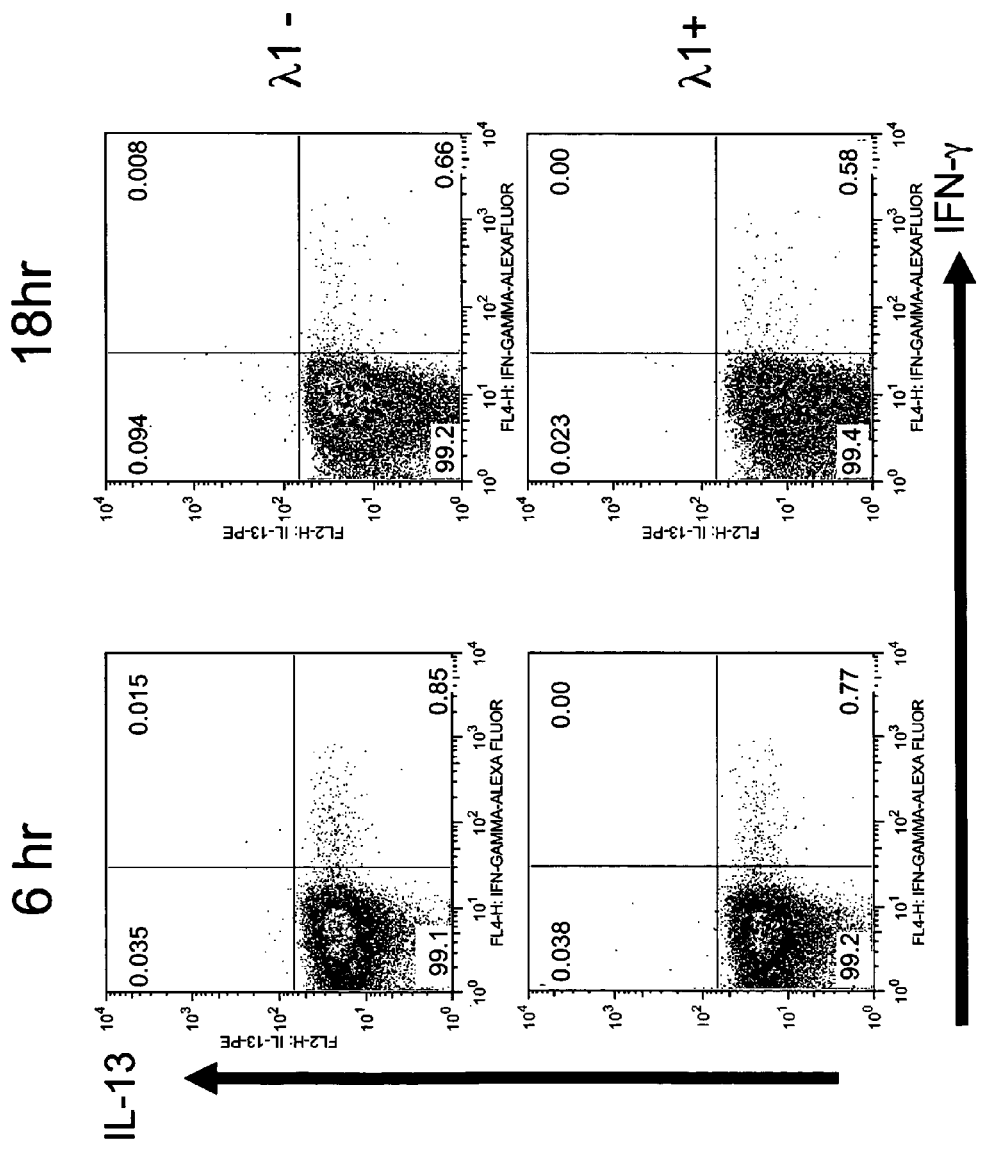

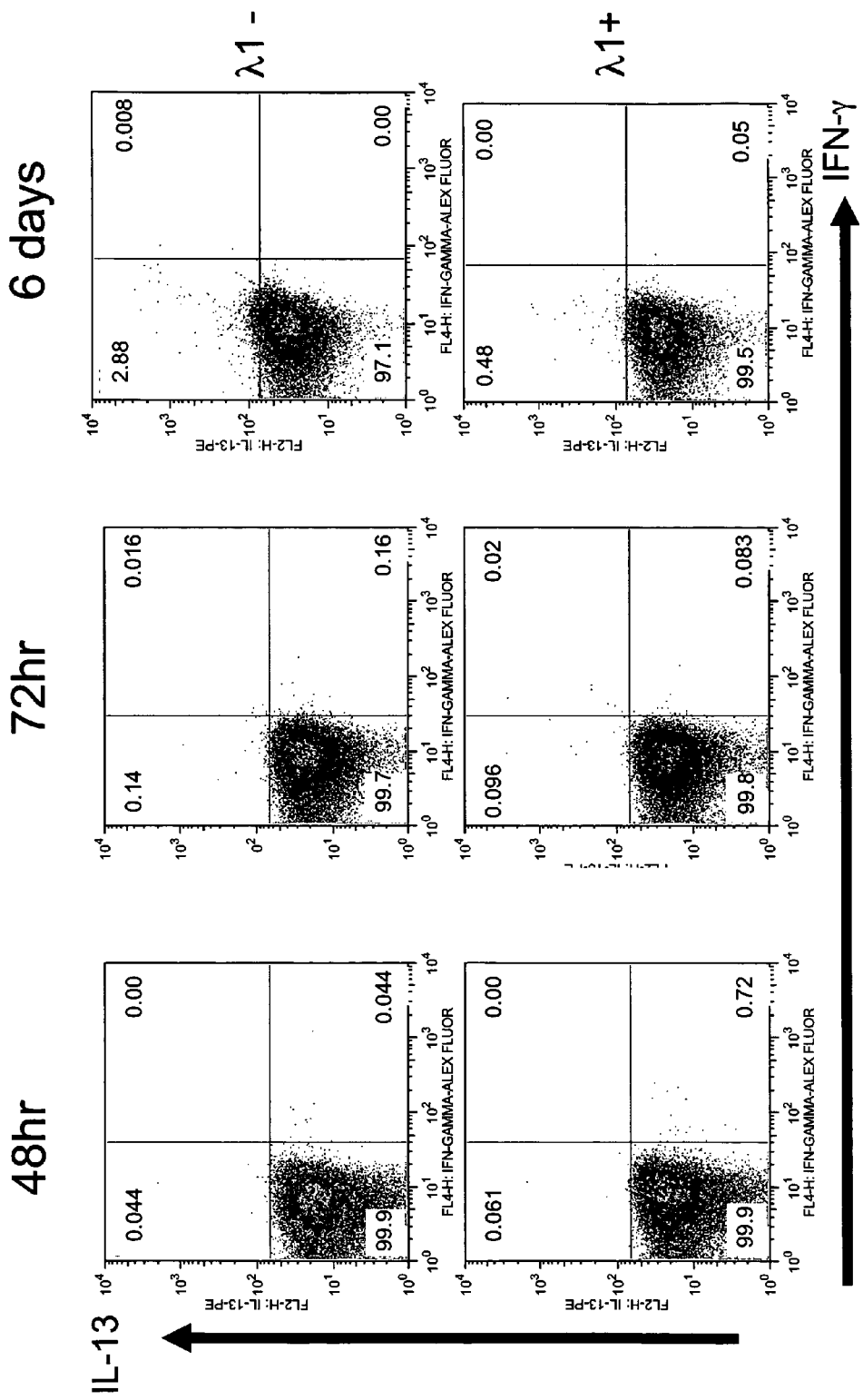
Fig. 3B, continued

EX-VIVO TREATMENT OF PERIPHERAL BLOOD LEUKOCYTES WITH IFN-λ

CROSS REFERENCE TO OTHER APPLICATION

The present application claims the benefit of priority to U.S. Provisional Application No. 60/983,168 filed Oct. 27, 2007, the entire disclosure of which is hereby incorporated by reference in its entirety.

FIELD OF THE INVENTION

The present invention generally relates to a method of ex vivo treatment of an immune cell by interferon lambda (IFN-λ). Specifically, the present invention provides a method of isolating peripheral blood leukocytes containing immune cells from a human subject, exposing the immune cells to IFN-λ at a concentration sufficient to reduce the production of specific cytokines (i.e., IL-4, IL-5 and IL-13), and administering the IFN-λ treated immune cells into the human subject. The ex vivo treatment may be combined with administration of IFN-λ. The present invention is applicable to patients having a Th2-associated disease such as asthma.

BACKGROUND OF THE INVENTION

Incidence of asthma and asthma-related disorders is increasing globally and in the developed world especially. According to a 2004 survey in the United States, asthma and related disorders resulted in almost 1.8 million emergency room visits, over 450,000 hospital admissions and 5,429 deaths. Asthma is directly responsible for approximately 15% of all pediatric emergencies (Cohn, Ann. Rev. Immunol., 2004; Barnes & Lemanske, New Engl. J. Med., 2001). The economic impact is high, estimated at ~$16 billion per year. These figures have been rising over the last 20 years. Thus, asthma constitutes a significant and growing medical problem in the United States in terms of morbidity and economic impact.

Triggered by airborne antigens such as pollens, viruses, fungi and bacteria, asthma involves a complex network of cytokines (Walker et al. J. Allergy Clin. Immunol., 1991). Accumulation of Th2 cells in the lung tissue is a key feature of asthma (Robinson et al., New Engl. J. Med., 1992). In the course of asthma, multiple cytokines are released from various cell types (e.g., epithelial cells, lymphocytes, mast cells and granulocytes) in the lung parenchyma. The released cytokines help to initiate and maintain asthma development. In experimental asthma models, airway hyper-reactivity is accompanied by high levels of IL-4 and IL-5. IL-4 appears to be essential for the development of Th2 responses in general (Mowen & Glimcher, Immunol. Rev., 2004), and animals genetically deficient in IL-4 (i.e., IL-4 knock-out mice) cannot be induced to develop allergic airway inflammation (Ray & Cohn, J Clin Invest., 1999).

Other evidence, however, suggests that IL-13, and not IL-4, seems to be a key cytokine to asthma pathogenesis in humans. In humans, asthma-specific T-cells produce IL-13, and IL-13 elevates mast-cell proliferation and induce IgE synthesis (Punnonen et al., Proc Natl Acad Sci USA., 1993). Sputa obtained from asthma patients are rich in IL-13 (Berry et al., J Allergy Clin Immunol., 2004). IL-13 mRNA and protein are expressed at a high level in the lungs of trigger-exposed human volunteers and asthma patients (Humbert et al., J Allergy Clin Immunol., 1997). Airway hyper-reactivity accompanied by high levels of IL-4, IL-5 and IL-13 can be induced in normal but not IL-13 −/− mice (Mattes et al., J. Immunol., 2001) Thus far, experimental therapeutic strategies to target Th2 cytokines which do not address IL-13 have failed (O'Byrne, Chest, 2006). Asthma-sensitized animals can be protected by blocking the cell-surface receptor for IL-13 (Taube et al., J. Immunol., 2002). IL-13 appears to be a contributing factor in the increased IL-4 and IL-5 levels. Once initiated, elevated levels of IL-4 and IL-5 are believed to exacerbate the asthmatic response.

An attempt was proposed to use IFN-λ in order to alleviate asthma. To this end, Davies et al. (WO 2007/029041) disclose the use of IFN-λ in virus-induced exacerbation of asthma. An aerosolized dose is recommended to bring IFN-λ in direct contact with the virus-infected airway epithelial cells. This group hypothesized that IFN-λ would eradicate the viral infection, thus alleviating the virus's ability to exacerbate the asthma. Viruses (such as respiratory syncytial virus (RSV) and rhinovirus (RV)) are known to infect airway epithelial cells, and the anti-virus effect of IFN-λ is believed to be maximized by the proposed airway delivery of IFN-λ. The half-life of IFN-λ may hinder the approach, as attempts are made to couple the IFN-λ, with polyethylene glycol (PEG) to extend its functional half-life and to present an alternative method of introducing IFN-λ, other than through expression of DNA constructs. However, the airway route does not guarantee IFN-λ, to come in contact with cytokine-producing lymphoid cells in lung parenchyma. The presence of an exceedingly thick mucus layer in asthmatic patients further hinders the success of this approach. While Davies et al. proposes a direct anti-virus effect by IFN-λ, the possible role of IFN-λ with Th2 cells in the lung, blood and lymphoid compartments and their secreted products (i.e., IL-4, IL-5, IL-13 cytokines, etc.), has not been addressed.

Intravenous delivery of IFN-λ is undesirable. Once administered, circulating IFN-λ may exert global side-effects on a human body. In addition, Th2 cytokine-producing cells in the lung parenchyma may be shielded from the systemic levels of IFN-λ. It is generally believed that intravenous administration IFN-λ is not ideal to combat asthma.

There is a continuing need to find an effective means to modulate Th2 cells in an attempt to blunt cytokine production. The present inventors surprisingly found that IFN-λ can directly modulate Th2 cells in affecting the cytokine release. Specifically, the present inventors discovered that ex-vivo treatment of peripheral mononuclear cells (including naïve and memory T-cells) blunts the production of IL-4, IL-5 and IL-13. Given that these cytokines contribute to an asthma response, the present inventors propose a method of alleviating asthma by ex-vivo treatment of human blood leukocytes with IFN-λ, followed by its administration into a human. It is believed that administration of IFN-λ-treated blood leukocytes will inhibit the human body from generating asthma-inducing Th2 cytokines, and thus alleviating the symptoms and root-cause of asthma.

SUMMARY OF THE INVENTION

In one aspect, the present invention provides a method of alleviating a Th2 disease, comprising the steps of: (a) identifying a patient having a Th2 disease; (b) isolating peripheral blood leukocytes containing immune cells from said patient; (c) exposing said immune cells to IFN-λ in an amount effective to reduce IL-4, IL-5 and IL-13 production from said immune cells when stimulated; and (d) administering said IFN-λ-exposed immune cells to said patient.

In another aspect, the present method may be used to treat peripheral mononuclear blood cells or fractionated cells enriched for a particular cell type, such as, for example naïve T-cells or memory T-cells.

The Th2 diseases to be alleviated by the present method include, but are not limited to, asthma, allergic bronchitis, interstitial lung disease, allergic airway disease, allergic rhinitis, and the like. Preferably, the Th2 disease is asthma. Asthma includes allergic asthma, intrinsic asthma, and occupational asthma.

The present method may employ a IFN-λ1, IFN-λ2, IFN-λ3 or a combination thereof. The cells that are used in this method may be peripheral mononuclear blood cells or a fraction of these cells enriched for a certain cell type, such as, for example, T-cells.

In yet another aspect, the present invention provides a method of ex vivo treatment, comprising the steps of: (a) obtaining peripheral blood from a human subject; (b) isolating mononuclear cells from said peripheral blood; (c) exposing said isolated mononuclear cells to IFN-λ; and (d) administering said exposed cells to said human subject, wherein said IFN-λ is in an amount sufficient to inhibit stimulus-induced cytokine release, and wherein said cytokine is selected from the group consisting of IL-4, IL-5 and IL-13 and said stimulus is selected from the group consisting of Concanavalin A and anti-CD2/3/28 beads. Preferably, IFN-λ is selected from the group consisting of IFN-λ1, IFN-λ2, IFN-λ3 and a combination thereof. Preferably, the mononuclear cells are T-cells. More preferably, the T-cells are naïve T-cells or memory T-cells.

In another aspect, the present invention provides an ex vivo treatment using IFN-λ in the concentration range about 1 ng/mL to about 200 µg/mL. Preferably, the concentration range is about 100 ng/mL to about 10 µg/mL.

In another aspect, the present invention provides an ex vivo treatment of IFN-λ for suitable duration sufficient to inhibit IL-4, IL-5 and IL-13 production. Preferably, the IFN-λ treatment is performed for about 1 hour to about 24 hours. Preferably, the treatment duration is about 6 hours to about 12 hours. More preferably, the treatment duration is about 6 hours.

In another aspect, the present invention provides an ex vivo treatment of immune cells with IFN-λ, where the immune cells used are in the range of about $1 \times 10^7$ cells to about $1 \times 10^9$ cells. Preferably, the immune cells are about $1 \times 10^8$ cells. Preferably, the ex vivo treatment of IFN-λ can be repeated by further exposing immune cells to IFN-λ.

In another aspect, the present method includes the step of administering IFN-λ-treated immune cells back into the human patients.

In yet another aspect, the present invention further provides co-administration of IFN-λ, in addition to the ex vivo treatment. Preferably, the IFN-λ treatment and ex vivo treatment may be performed simultaneously or sequentially. Preferably, IFN-λ treatment may be performed within 24-48 hours after ex vivo treatment.

BRIEF DESCRIPTION OF THE DRAWINGS

FIG. 3B shows that IFN-λ reduced the numbers of cytokine positive CD4 T-cells. The Time Course Study shows IL-13$^+$ and IFN-γ$^+$ cells with and without added IFN-λ. Top row, FACS analysis of cells not treated with IFN-λ, over 6 hours, 18 hours, 48 hours, 72 hours and 6 days; bottom row, FACS analysis of cells treated with IFN-λ over 6 hours, 18 hours, 48 hours, 72 hours and 6 days.

FIG. 8A shows expression of IL-4Rα on freshly isolated memory CD4$^+$ T-cells following stimulation with anti-CD2/3/28 beads. Following bead stimulation, only naïve T-cells express IL-4Rα, which was down-regulated by IFN-λ.

FIG. 11B shows that IFN-λ prevented the activation-induced down-regulation of CD62L under both neutral and Th2 conditions on memory CD4+ T-cells. Bead activation induced down-regulation of CD62L. IFN-λ significantly prevented the activation-induced differentiation of memory cells.

Figure 12:
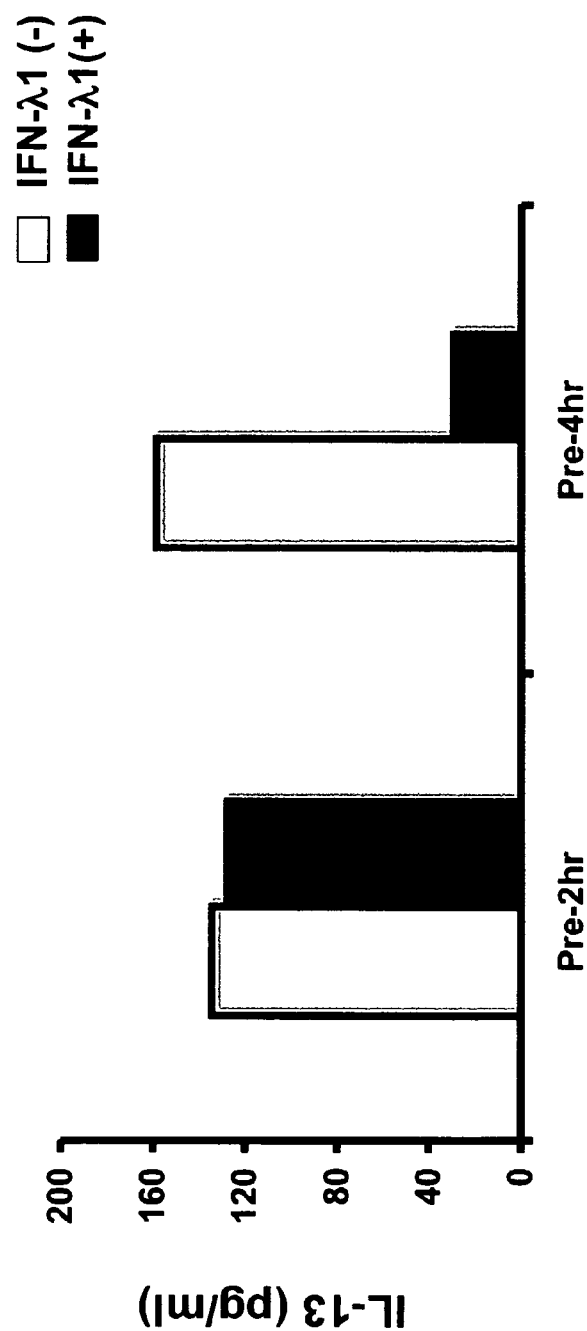

FIG. 12 shows that IFN-λ pre-treatment of PBMC inhibited the release of IL-13. PBMC were isolated and pre-treated with IFN-λ. Treated PBMC were washed followed by stimulation with anti-CD2/3/28 coated beads for 3 days. IFN-λ pre-treatment of 4 hours blocked the IL-13 production at day 3.

DETAILED DESCRIPTION OF THE INVENTION

All patents, patent applications, published literature and citations to the NCBI database Accession Numbers cited herein are incorporated by reference in their entirety including all amino acid sequence data therein.

Standard reference works setting forth the general principles of recombinant DNA technology known to those of skill in the art include Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HANDBOOK OF MOLECULAR AND CELLULAR METHODS IN BIOLOGY AND MEDICINE, CRC Press, Boca Raton, 1995; McPherson, Ed.

Definitions:

As used herein, the term "interferon lambda" (i.e., IFN-λ) are used interchangeably to describe a family of proteins that include IFN-λ1 (IL-29); IFN-λ2 (IL-28A); IFN-λ3 (IL-28B). For purposes of this application, IFN-λ is intended to encompass all members of the IFN-λ family including, for example, IFN-λ1, IFN-λ2, and IFN-λ3 and the variants thereof insofar as these molecules function equivalently in the methods of the invention in inhibiting cytokine production of IL-4, IL-5 and IL-13 from immune cells.

The amino acid sequences of IFN-λ are known. The three IFN-λ polypeptide sequences have been disposited in GenBank. The respective amino acid sequences are set forth as follow:

As used herein, the term "human subject" refers to a human at risk of, or suffering from, asthma or IBD. Guidelines for diagnosing asthma are known in the art; for example, Global Initiative for Asthma has provided a guideline publication (see, ginasthma.com). For purposes of the present invention, the invention may also be used in mammals other than human, such as domestic animals (e.g., dog, cat, and the like) as well as experimental animals (e.g., mouse, rabbit, and the like).

As used herein, the term "ex vivo" refers to a condition that takes place outside an organism. Specifically, treatment of immune cells ex vivo means exposing such cells to IFN-λ in an artificial environment (sterile conditions) outside the organism with the minimum alteration of the natural conditions. This procedure involves culturing mononuclear cells that have been isolated from a human prior to administration back into the same human subject.

As used herein, the term "Th1 disease or disorder" refers to a pathological state in which a Th1 response contributes to the pathology. In Th1 disease, Th1-type cytokines tend to produce the pro-inflammatory responses responsible for killing intracellular parasites and for perpetuating autoimmune responses. Interferon gamma is the main Th1 cytokine. Excessive pro-inflammatory responses can lead to uncontrolled tissue damage.

As used herein, the term "Th2 disease or disorder" refers to a pathological state in which a Th2 response contributes to the pathology. In Th2 disease, Th2-type cytokines include IL-4, IL-5, and IL-13, which are associated with the promotion of IgE and eosinophilic responses in atopy, which has more of an anti-inflammatory response. Th2 responses will counteract the Th1 mediated microbicidal action. The optimal scenario to maintain a health condition would be that humans should produce a well balanced Th1 and Th2 response, suited to the immune challenge.

As used herein, the term "asthma" includes various disorders of the airway, including, for example, asthma, allergic rhinitis and chronic obstructive pulmonary disorder. For purposes of this application, asthma is intended to encompass various forms of asthma including intrinsic asthma, allergic asthma, allergic airways disease, allergic bronchopulmonary

```
IFN-λ1: GenBank Accession No: Q8IU54 (SEQ ID NO: 1)
MAAAWTVVLV  TLVLGLAVAG  PVPTSKPTTT  GKGCHIGRFK  SLSPQELASF   50

KKARDALEES  LKLKNWSCSS  PVFPGNWDLR  LLQVRERPVA  LEAELALTLK  100

VLEAAAGPAL  EDVLDQPLHT  LHHILSQLQA  CIQPQPTAGP  RPRGRLHHWL  150

HRLQEAPKKE  SAGCLEASVT  FNLFRLLTRD  LKYVADGNLC  LRTSTHPEST  200

IFN-λ2: GenBank Accession No: Q8IZJ0 (SEQ ID NO: 2)
MKLDMTGDCT  PVLVLMAAVL  TVTGAVPVAR  LHGALPDARG  CHIAQFKSLS   50

PQELQAFKRA  KDALEESLLL  KDCRCHSRLF  PRTWDLRQLQ  VRERPMALEA  100

ELALTLKVLE  ATADTDPALV  DVLDQPLHTL  HHILSQFRAC  IQPQPTAGPR  150

TRGRLHHWLY  RLQEAPKKES  PGCLEASVTF  NLFRLLTRDL  NCVASGDLCV  200

IFN-λ3: GenBank Accession No: Q8IZ19 (SEQ ID NO: 3)
MKLDMTGDCM  PVLVLMAAVL  TVTGAVPVAR  LRGALPDARG  CHIAQFKSLS   50

PQELQAFKRA  KDALEESLLL  KDCKCRSRLF  PRTWDLRQLQ  VRERPVALEA  100

ELALTLKVLE  ATADTDPALG  DVLDQPLHTL  HHILSQLRAC  IQPQPTAGPR  150

TRGRLHHWLH  RLQEAPKKES  PGCLEASVTF  NLFRLLTRDL  NCVASGDLCV  200
``` aspergillosis, allergic bronchitis, occupational asthma, reactive airway disease syndrome, interstitial lung disease, and the like.

As used herein, the term "inhibit" refers to a decrease or elimination of the referenced parameter. The terms "treatment" and "inhibition" are used interchangeably in this application. For example, when an immune cell is stimulated with an agonist such as Concanavalin A or anti-CD2/3/28 engagement, cytokine production (e.g., IL-13) is elevated. However, when pre-treated with IFN-λ, the immune cell's production of IL-13 is decreased or eliminated.

As used herein, the term "peripheral blood mononuclear cells" (i.e., PBMC) is used interchangeable with "immune cells." PBMC is intended to encompass T-cells, B-cells, monocytes, and natural killer cells, all of which are characterized as having a single nucleus. PBMC can be conveniently obtained from human peripheral blood using a density-gradient centrifugation technique. ~70% of PBMC is T-cells, of which ~50% is naïve T-cells and ~50% is memory T-cells.

As used herein, the term "stimulus-induced" refers to using a T-cell stimulus that induces T-cell activation. Exemplary stimuli include, but are not limited to, mitogens such as Concanavalin A, and anti-CD2/3/28 beads.

As used herein, the term "T-cells" refers to a subset of lymphocytic cells (matured in thymus) that are present in PBMC and express a surface marker of CD3 (T-cell receptor). T-cells is intended to include $CD4^+$ (i.e., T-helper cells) and $CD8^+$ (i.e., cytotoxic killer cells).

As used herein, the term "naïve T-cell" is a T cell that has differentiated in bone marrow, and successfully undergone the positive and negative processes of central selection in the thymus. A naive T cell is considered mature, but is distinguished from activated T-cells or memory T-cells, as it is thought not to have yet encountered cognate antigen in the periphery.

As used herein, the term "memory T-cell" is a specific type of infection-fighting T cell that can recognize foreign invaders such as bacteria or viruses that were previously encountered by the cell during a prior infection or vaccination. At a second encounter with the invader, memory T-cells can reproduce to mount a faster and stronger immune response than the first time the immune system responded to the invader.

As used herein, the term "untouched" refers to cells that have not been bound by an antibody during cell isolation. Cell isolation often employs antibody to either positively or negatively select cells of interest. An "untouched" naïve T-cell refers to an isolated naïve T-cell that such antibody-isolation protocol is not employed (i.e., the isolated naïve T-cell has not been exposed to an antibody during the cell isolation).

As used herein, the term "GATA3" and "T-bet" refer to transcription factors in cells. GATA3 is recognized to participate in the transcription of multiple genes whose proteins are known to promote a Th2 response. T-bet is recognized to participate in the transcription of genes whose proteins are known to promote Th1 response.

As used herein, the term "CD62L" refers to L-selectin. CD62L is known to be present on lymphocytes and is thought to be important in lymphocyte trafficking from the blood compartment into the lymph compartment via the high endothelial venules.

The present inventors surprisingly discovered that T-cells possess an IFN-λ, receptor and that the T-cell function can be modulated by IFN-λ. To the best of inventors' knowledge, the present invention represents the first observation that IFN-λ can down-regulate the secretion of Th2 cytokines such as IL-4, IL-5 and IL-13 in peripheral blood mononuclear cells. The present inventors discovered that this down-regulation of cytokine secretion is accomplished by a reduction in IL-4 and IL-13 mRNA and a decrease in the numbers of IL-4 and IL-13 positive $CD4^+$ T-cells. The present application relates to the discovery that IFN-λ decreases multiple Th2 cytokines, including IL-4, IL-5 and IL-13.

Accordingly, the present invention provides a method for treating the immune cells in an asthmatic patient with IFN-λ to down-regulate Th2 cytokines (e.g., IL-13, IL-4 and IL-5) in an attempt to ameliorate the severity of asthmatic diseases driven by a Th2 response. Such asthmatic diseases include, for example, allergic respiratory disorders, allergen-induced asthma and the like.

In one embodiment, the present method employs ex vivo treatment of peripheral blood mononuclear cells with IFN-λ. Those skilled in the art would appreciate that there are many established protocols for isolating PBMC from peripheral blood. Human peripheral blood may be drawn conveniently via venipuncture. Isolation of PBMC may be aided by density-gradient separation protocols, usually employing Ficoll-Hypaque or Histopaque. The PBMC isolation is performed under sterile conditions. Alternatively, cell elutriation methods may be employed to separate mononuclear cell populations. The advantages of the cell elutriation method include sterility and efficiency.

Isolated mononuclear cell populations include the lymphocytes such as T-cells. T-cells are often classified to include "helper" T-cell and "cytotoxic" T-cells, through the mutually-exclusive expression of the cell surface markers CD4 and CD8, respectively. It has become apparent that the T-helper response can itself be divided, according to whether it was polarized to support the development of hypersensitivity and antibody responses (i.e., "T-helper 2" or "Th2" cells) or cell-mediated responses (i.e., "T-helper 1" or "Th1" cells). These polarized T-cells were defined according to certain signature cytokines produced upon stimulation. For example, Th1 cells produce IL-2 and IFNγ, while Th2 cells produce IL-4, IL-5 and IL-13. Th1 and Th2 cells each arise from a precursor population (i.e., Th0 cell). Polarization to either Th1 or Th2 begins after activation through the T-cell receptor and is dependent upon signals received by the naïve T-cell. For example, if the T-cell is activated in the presence of IL-12, then the Th0 cell begins a process of Th1 maturation, wherein the IL-4 receptor ceases to be expressed on the surface, locking the cell to a Th1 pathway through activation of genes regulated by STAT-4, IFN regulatory and T-bet transcription factors. Conversely, cells activated in the presence of IL-4 down-regulate the IL-12 receptor and enter the Th2 pathway, activating the STAT-6, c-maf and GATA-3 transcription factors. In general, 100 ml of human peripheral blood can yield about $1 \times 10^8$ PBMC.

In one embodiment, the present invention relates to using IFN-λ to treat immune cells that are isolated from peripheral blood from a human. IFN-λ is a member of the Type-III interferon family which contains three members: namely, IFN-λ1, IFN-λ2 and IFN-λ3. The present method encompasses the use of any one of the three IFN-λ members or combinations thereof. These three proteins use the same unique hetero-dimeric receptor, comprised of the CRF2-12 (IFN-λ R1/IL-28Rα) chain and the CRF2-4 (IL-10-R-β) chains. As far as can be determined, IFN-λ, IFN-λ2 and IFN-λ3 are functionally synonymous. This receptor pair is not used by any other known ligand, although the CRF2-4 chain is also part of the IL-10, IL-22 and IL-26 receptors. Like their close relatives the Type-I interferons, IFN-λ1, IFN-λ2 and IFN-λ3 promote the phosphorylation of STAT1 and STAT2, induce the ISRE3 complex, elevate OAS and MxA expression, and exhibit an anti-viral activity in vitro.

Treatment of mononuclear cells with IFN-λ must be performed under strict sterile conditions. Freshly isolated mononuclear cells ($1\times10^7$-$1\times10^9$ cells) are suspended in suitable culture medium to achieve a suitable cell concentration of $1\times10^6$-$1\times10^7$ cells/ml. Exemplary media include RPMI and the like; optionally, the media may contain 2-10% heat-inactivated human serum albumin. IFN-λ is added to the culture media and incubation may be performed at a range of temperatures (e.g., 4° C., 25° C. or 37° C.). Preferably, the IFN-λ treatment occurs at 37° C. Suitable treatment duration can be conveniently optimized by one of ordinary skill in the art. Preferred treatment time includes 1 hour to 24 hours. More preferred treatment time includes 6 hours to 12 hours. Exemplary IFN-λ treatment doses include about 1 ng/ml to about 200 µg/ml. Preferably, the IFN-λ may be present at a concentration dosage of about 100 ng/ml to about 10 µg/ml.

One of skilled in the art would easily determine the optimal amounts of IFN-λ. An optimal amount of IFN-λ that is effective in inhibiting stimulus-mediated release of IL4, IL-5 and IL-13 from the mononuclear cells can be determined by established ELISA protocols. IFN-λ treated T-cells may then be reintroduced back into the human patient. Without being bound by any particular theory, it is believed that the IFN-λ treated mononuclear cells, when in the human body, have the diminished capability to produce IL-4, IL-5 and IL-13.

Optionally, IFN-λ treated cells may be washed prior to administering into the same human subject from which the mononuclear cells were isolated (i.e., autologous). Washing medium is exemplified by PBS, HBSS, RPMI and the like. Without bound by a theory, washing procedure may remove any cell-released cytokines (e.g., IL-8) that may exert adverse effects in the human host body. Ideally, only the IFN-λ treated cells are administered back into a human. One of ordinary skill in the art would recognize that administering of cells in a human requires strict sterility conditions. Optimal amount of IFN-λ treated mononuclear cells may be administered. In one embodiment, $1\times10^7$-$1\times10^9$ mononuclear cells are treated with IFN-λ, and are administered back into patients. Preferred, $1\times10^8$ cells mononuclear cells are used. Administering can be performed conveniently with the use of an intravenous infusion tubing. Infusion may either be a bolus infusion or continuous infusion over a suitable time (e.g., 1 hour). Suitable infusion medium includes dextrose, saline or the like as known in the art.

The present invention utilizes the novel observation that IFN-λ has potent effects on Th2 responses by inhibiting the production of Th2 cytokines. Asthma disease is marked by an imbalance of Th1 or Th2 response (i.e., an elevated Th2 response) that actually leads to its exacerbation. For example, although asthma development is multi-factorial, Th2 cytokines are highly associated with the disease, especially IL-4, IL-5 and IL-13, secreted following antigen challenge in allergic asthma. Susceptibility to asthma in humans has been linked to the IL-4/IL-5/IL-13 locus on chromosome 5. In murine asthma models, airway hypersensitivity develops upon transfer of antigen-specific Th2, but not Th1 cells and IL-4$^{-/-}$ mice do not develop an allergic inflammatory response after airway challenge. In another embodiment, the present invention provides an ex vivo treatment of immune cells with IFN-λ followed by administering of IFN-λ treated immune cells back into the human, thereby inhibiting the immune cells' production of Th2 cytokine and thus alleviating the development and symptoms of asthma. Accordingly, the present invention is based on the premise that influencing the Th2 response in an asthmatic disease is beneficial to the outcome of disease.

The present inventors discovered that IFN-λ exerts potent immuno-modulatory effects on T-cells and their cytokine release during the Th1/Th2 T-cell responses.

One of ordinary skill in the art would conveniently assess if administration of IFN-λ-treated cells may improve a patient's asthmatic response. Standard Pulmonary Function Tests may be performed to determine if there is an improvement in lung function following administering of IFN-λ cells. One example includes the spirometry test where a spirometer is used to create a volume-time curve or flow-volume loop. The most commonly used guidelines for spirometric testing and interpretation are set by the American Thoracic Society. With the aid of a spirometer, pulmonary tests (e.g., Forced Vital Capacity (FVC) and Forced Expiratory Volume in 1 second ($FEV_1$)) can be measured. FVC represents the total amount of air that can forcibly be blown after full inspiration, measured in liters, and $FEV_1$ represents the amount of air that one can forcibly blow in one second, measured in liters. The ratio of $FEV_1$ to FVC provides an index if improved respiratory function occurs. A healthy adult has a $FEV_1$ to FVC value of ~75-80%.

The effectiveness of ex vivo treatment may be alternatively assessed by a diminution of blood Th2 cytokines (e.g., IL-13) level after administering of IFN-λ cells. The concentration of cytokines such as IL-13 can be conveniently assayed by an ELISA. Lung lavage fluid may also be obtained from a patient following IFN-λ-treated cell administration. Levels of Th2 cytokines (e.g., IL-13) may be determined by an ELISA. Other indications of improvement may include a decreased mucus production in the airway and morphological assay to verify a lesser bronchial inflammation (e.g., reduced infiltration of Th2 inflammatory cells into the airway of a patient). All of these parameters can be used individually or in combination to assess the effectiveness of ex vivo treatment. Based on this information, one of ordinary skill in the art would easily determine if an additional ex vivo treatment may be needed.

In yet another embodiment, PBMC can further be fractionated to enrich for T-cells. Furthermore, naïve T-cells and memory T-cells can be further purified using standard protocols, such as negative selection protocol using magnetic beads. The isolated T-cells, naïve T-cells, or memory T-cells can be treated with an effective amount of IFN-λ. An effective amount is an amount of IFN-λ that causes a reduction in the levels of IL-13, IL-4 and IL-5 in PBMC, naïve T-cells or memory T-cells.

In one embodiment, the mononuclear cells are further fractionated into T-cells and treated with an effective amount of IFN-λ. IFN-λ treated T-cells are then returned to the human patient. In another embodiment, naïve T-cells or memory T-cells are isolated and also treated with an effective amount of IFN-λ and returned to the human patient. Without being bound by any particular theory, it is believed that the IFN-λ, treatment of T-cells, naïve T-cells, or memory T-cells is effective in inhibiting production of IL-4, IL-5, and IL-13 in the human patient.

The present invention encompasses various allelic variants of IFN-λ polypeptides insofar as they would inhibit the IL-4, IL-5 and IL-13 production and release, like that of a naturally-occurring IFN-λ polypeptides. The present invention also encompasses all three members of the IFN-λ: namely, IFN-λ1, IFN-λ2, and IFN-λ3.

In another embodiment, a human patient is treated ex vivo. Such a method comprises identifying a human patient in need of treatment (e.g., an asthmatic patient having a Th2 disease); removing PBMC from the patient and treating the PBMC with an effective amount of IFN-λ, and returning treated PBMC to the human patient. An effective amount will be an amount that causes a reduction in IL-13, IL-4 and IL-5 levels from the PBMC. The treated cells, when introduced back into the patient, provide relief of symptoms of the disease or disorder being treated.

The present method utilizes the novel observation that IFN-λ prevents the loss of homing receptor from T-cells (i.e., naïve and memory T-cells). Specifically, IFN-λ treatment inhibits the shedding of L-selectin (i.e., CD62L). L-selectin on T-lymphocytes plays a role in homing (i.e., transmigration from blood vessels into lymphatic vessels and further into lymph nodes). If L-selectin on T-cells is prevented from shedding, it would allow T-cell to undergo firm adhesion and transmigration. Once migrated into lymphoid tissue, L-selectin on T-cells is necessary for its homing into lymph nodes, where T-cells interact with dendritic cells and receive information therefrom.

Without wishing to be bound by a theory, the present inventors believe that IFN-λ's effect on blockade of L-selectin shedding in T-cells would alleviate symptoms associated with asthma (e.g., less mucus formation and eosinophil infiltration). By preventing L-selectin from shedding, IFN-λ treated T-cells can swiftly migrate into lymphoid organs. IFN-λ prevents Th2 cytokine-producing T-cells from being sequestered in asthmatic tissues (i.e., inflamed airways). With intact L-selectin, IFN-λ treated T-cells are expected to follow their normal migratory paths (i.e., migrate into lymphatic tissues and into lymph nodes). The IFN-λ treated T-cells are further expected to stay in the lymphoid tissues for a longer duration prior to their re-entry into the blood vessels. In the absence of IFN-λ treatment, T-cells would shed the L-selectin and accumulate into asthmatic inflamed tissues. As such, IFN-λ treatment is advantageous in that there is less expected infiltration of T-cells into asthmatic tissues. Notably, less T-cell infiltration translates into reduced local accumulation of IL-13 in inflamed airways.

IFN-λ also renders the T-cells to be less responsive to stimuli in terms of Th2 cytokine release. The combined effect of IFN-λ on T-cells is believed to be advantageous to alleviate the symptoms of asthma.

In one embodiment, the present invention includes a combined treatment, whereby a human patient is treated ex vivo of mononuclear cells or T-cells, and a co-administration of IFN-λ. Accordingly, the present ex vivo method may be used in combination with IFN-λ administration.

In one embodiment, the ex vivo method is first performed. Specifically, PBMC from a human patient in need of treatment are isolated. The isolated PBMC are treated with an effective amount of IFN-λ, followed by administering the IFN-λ treated PBMC back into the same human patient (i.e., autologous). Then, a second administration of IFN-λ will be performed with the same human subject. The second IFN-λ administration may be performed simultaneously, separately or sequentially with the ex vivo method (i.e., before or after the administration of ex vivo IFN-λ treated PBMC).

In one embodiment, the second administration of IFN-λ may be performed systemically, nasally, or orally. Alternative routes of administration include, but are not limited to, intranasal, subcutaneous and parenteral administration. IFN-λ may be administered alone or in admixture with a pharmaceutically acceptable carrier. The IFN-λ formulations may be provided using any formulation known in the art and appropriate for the route of administration. Such formulations may be as provided using the guidance of such resources as *REMINGTON'S PHARMACEUTICAL SCIENCES*, 18th ed., Mack Publishing Co., Easton, Pa. 1990. Exemplary formulation may include a solution that is isotonic with blood such as saline, Ringer's solution, or dextrose solution. Alternatively, non-aqueous vehicles such as fixed oils and ethyl oleate may be used, as well as liposomes. IFN-λ may conveniently be in the form of an aerosol spray. The spray may be coupled with a pressurized container, pump, or nebulizer with the use of a suitable propellant. Exemplary propellants include, but are not limited to, dichlorodifluoromethane, trichlorofluoromethane, hydrofluoroalkane and the like. The spray may contain ethanol and lubricants (e.g., sorbitan trioleate). It is appreciated that the daily dose with an aerosol will vary from patient to patient, and may be administered in a single dose or in divided doses.

Further, excipients may be included that improve the efficacy, receptor affinity, or half-life of the active ingredient. For example, but not by way of limitation, the IFN-λ of the methods of the invention may be pegylated (i.e., coupled with polyethylene glycol) by means well-known in the art to prolong the half-life of the active ingredient in the circulation. (See, e.g., Kozlowski et al. J. Control Release 72: 217-224, 2001). Such modification may enhance biological activity to be useful as therapeutic agents.

In one embodiment, the ex vivo IFN-λ treated immune cells are returned to the human intravenously and a second dose of IFN-λ is administered parenterally. The IFN-λ treated immune cells can be infused back into human via a bolus injection intravenously. Alternatively, the injection can be performed slowly over the course of hours. The IFN-λ parenteral administration can be performed intradermally, intranasally, etc. Preferably, the administering of ex vivo IFN-λ treated cells may occur simultaneously with the second dose of IFN-λ administration. In one embodiment, the administrations may be repeated.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

Materials and Methods

I) Human Subjects

Human peripheral blood mononuclear cells (PBMC) were isolated from buffy coats purchased from the Newark Blood Bank (Newark N.J.). These buffy coats were completely anonymous and it was not possible to identify the donors. PBMC were isolated by density-gradient centrifugation over Histopaque-1077 (Sigma, St. Louis).

II) Cell Preparation

PBMC were harvested by density gradient centrifugation over Histopaque within 24 hours of sampling. Cells were collected and washed twice in RPMI 1640 medium (Invitrogen, Grand Island, N.Y.). The cells were finally re-suspended at a final concentration of $1\times10^6$/mL in RPMI 1640 medium supplemented with 10% heat-inactivated fetal calf serum (FCS; GIBCO).

III) T Cell Subsets Isolation

"Untouched" naïve $CD4^+$T-cells ($CD3^+CD4^+CD45RA^+$ $CD45RO^-$) and memory $CD4^+$T-cells ($CD3^+CD4^+$ $CD45RO^+$) were prepared from PBMC using negative magnetic separation kit (Stemcell Tech), according to the manufacturer's instructions. In brief, freshly isolated PBMC were incubated (room temperature, and 20 min.) with a cocktail of antibodies against CD8, CD14, CD16, CD19, CD20, CD36, CD56, CD123, TCRγ/δ, and glycophorin A (See, FIG. 5). Dextran-coated magnetic nanoparticles microbeads were added. Magnetically labeled cells were separated from unlabeled cells using a magnet device. The unlabeled cells constitute the memory T-cells. For naïve T-cell isolation, PBMC were incubated with biotinylated anti-CD45RO antibody first, followed by the addition of the cocktail of antibodies (i.e., CD8, CD14, CD16, CD19, CD20, CD36, CD56, CD123, TCRγ/δ, and glycophorin A). Separation of unlabeled cells (i.e., naïve T-cells) was performed as described above. The purities of the both memory T-cell and naïve T-cell populations were determined to be >95% (See FIG. 6A).

IV) Cell Culture Condition

After washing, cells were adjusted to density of $1 \times 10^6$ cells/ml per well in 24-well flat-bottom plates. Cells were stimulated with microbeads coated with anti-CD2/CD3/CD28 ("beads", $5 \times 10^5$/ml, bead-to-cell ratio 1:2, Miltenyi biotech Inc., CA) in the presence or absence of 100 ng/ml IFN-λ1 (Peprotech, NJ), in 1 ml cultures. For Th2 cell polarization, naïve CD4$^+$ T-cells were cultured in Th2 condition with CD2CD3CD28beads+10 ng/ml of IL-4 (Peprotech, N.J.). Supernatants were harvested at different time points as indicated, while cells were stored at −80° C. in lysis (Stratagene, CA) buffer for RNA extraction. RPMI-1640 culture medium supplemented with 10% (v/v) heat-inactivated fetal calf serum was used throughout (complete medium).

V) Immunophenotype Analysis by Flow Cytometry

For immunophenotype analysis, PBMC, purified naïve or memory CD4$^+$ T-cells were quadruple stained with fluorescent-conjugated (FITC) mAbs specific for cell surface markers and analyzed by flow cytometry using a FACSCalibur™. FITC-labeled anti-CD3, PE-labeled anti-CD45RA, PE-labeled anti-CCR7, PECy5.5-labeled anti-CD4 were purchased from eBioscience. FITC-labeled anti-lineage124 (IL-4Rα), PECy5-labeled anti-CD62L, APC-labeled anti-CD45RO were purchased from BD PharMingen. For surface staining, cells were incubated with the respective mAbs at 4° C. in the dark for 30 minutes. The cells were thereafter washed twice and fixed in 0.5% paraformaldehyde before acquisition.

VI) Quantitation of Secreted Cytokine by ELISA

Levels of accumulated IFN-γ and IL-13 were determined by ELISA from 24 hours and 3 day cultures. Antibody pairs for IFN-γ were purchased from eBioscience (CA) and for IL-13, from R&D Systems (MN). Manufacturers' protocol was followed and all washes were performed with phosphate-buffered saline (PBS) containing 0.05% (v/v) Tween-20 (Sigma). Briefly, flat-bottom, 96-well plates were coated with the appropriate capture antibody and incubated at 4° C. overnight in the dark. After washing, plates were blocked with 1% (w/v) bovine serum albumin (BSA; Sigma) then standards and culture supernatants were plated in triplicate. After incubation at 37° C. for 2 hrs, plates were washed, exposed to first relevant biotinylated antibodies, then streptavadin-conjugated horse-radish peroxidase and finally to the chromogen, TMB. After 20 minutes, the reaction was halted by addition of sulphuric acid and the optical density at 450 nm determined. Cytokine concentrations were calculated from the standard curve present on each plate.

VII) Real Time Quantitative RT- PCR Analysis

Total RNA was extracted from cells (Stratagene CA) and cDNA prepared and subsequently assayed using a two-step procedure ("AffinityScript", Stratagene, CA). Quantitative (real-time) RT-PCR (qRTPCR) was carried out using a SYBRA Green method in a Stratagene MX-3000 instrument. cDNA samples were amplified thus: 10 minutes at 95° C. then 40 cycles of 95° C. 30 s, 60° C. 60 s, 72° C. 30 s. A melting curve analysis was carried out to verify that the Ct values were based upon a single PCR product. All primer concentrations were at 300 nM, except those for EF-1α (150 nM).

```
Primer pairs for cytokine analysis were:
IL-28RαF  5' CCA GCC AGT CCA GAT CAC TCT 3'
              (SEQ ID NO: 4)

IL-28RαR  5' ACA GCA GTA TCA GAA GCG ATG G 3'
              (SEQ ID NO: 5)

T-betF    5' ACC ACC TGT TGT GGT C 3'
              (SEQ ID NO: 6)

T-betR5'  5' CCT TTC CAC ACT GCA C 3'
              (SEQ ID NO: 7)

GATA3F    5' TCA AGG CAA CCA CGT C 3'
              (SEQ ID NO: 8)

GATA3R    5' GAT GGA CGT CTT GGA G 3'
              (SEQ ID NO: 9)

Relative levels of these cDNAs and the effect
of IFN-λ1 were established using the ΔΔCt
method against the housekeeping gene EF-1α:
EF-1αF    5' CTG AAC CAT CCA GGC CAA AT 3'
              (SEQ ID NO: 10)

EF-1αR    5' GCC GTG TGG CAA TCC AAT 3'
              (SEQ ID NO: 11)
```

VIII) Proliferation of CFSE-Labeled Naïve and Memory CD4+ T-Cells

Purified naïve or memory CD4$^+$T-cells were re-suspended in complete RPMI 1640 medium at $10^7$ cells/mL. Carboxyfluorescein diacetate succinimidyl ester (CFSE; Invitrogen, Carlsbad, Calif.) was added at a final concentration of 5 μM, and the cells were incubated for 10 minutes at 37° C. in 5% $CO_2$. The stain was quenched using 5 times the volume of ice-cold complete RPMI 1640 medium for 5 minutes. The cells were then washed 3 times and re-suspended in complete RPMI 1640 medium before stimulating them with CD2CD3CD28 beads. After 6 days of culture, cells were acquired with FACSCalibur and analyzed using FlowJo software.

EXAMPLE 1

Stimulation of Peripheral Blood Mononuclear Cells Causes Specific Cytokine Transcription: IFN-λ, Lowers the mRNA Levels for IL-4 and IL-13

Figure 1:
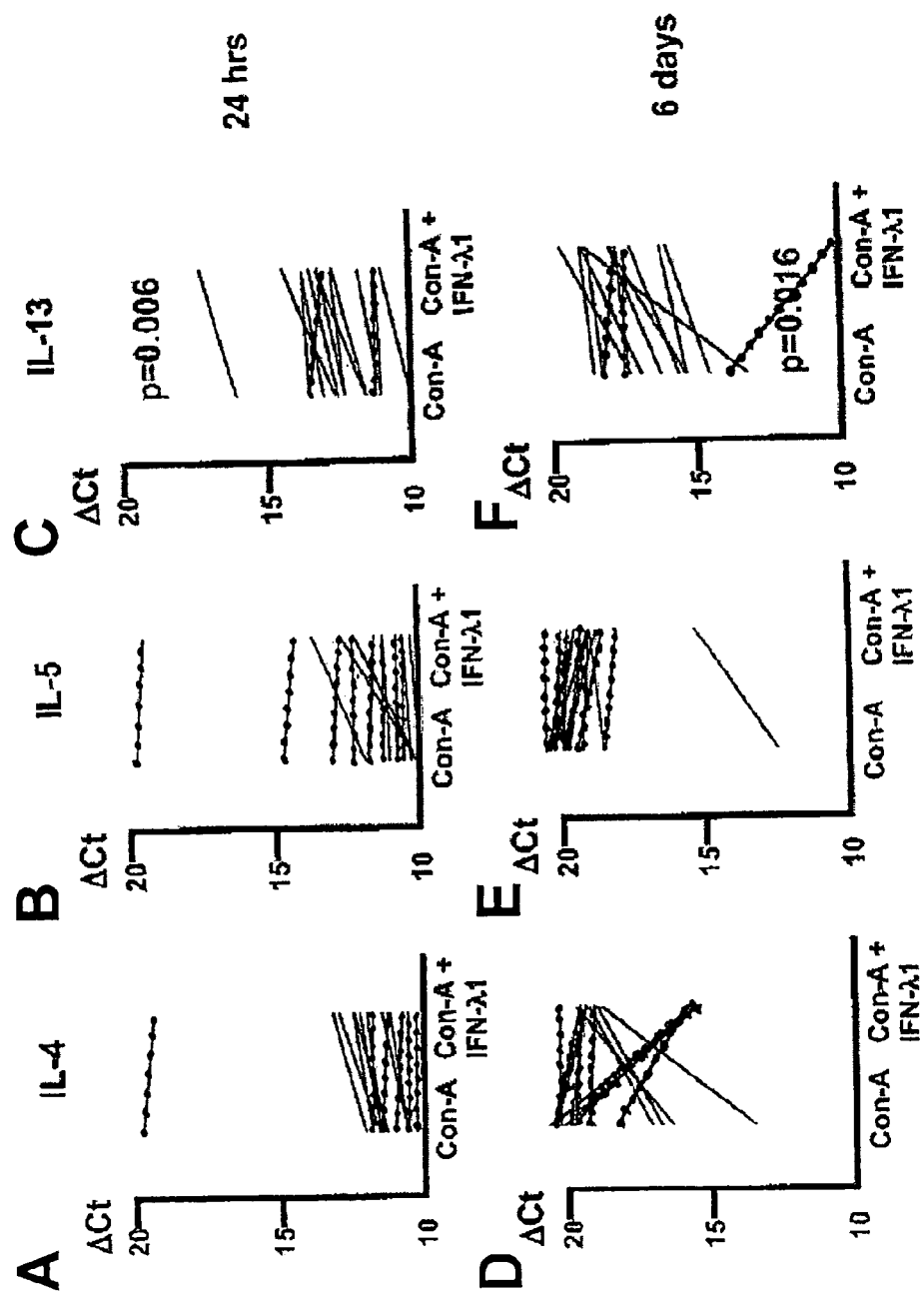
FIG. 1 shows that IFN-λ lowers the IL-4 and IL-13 mRNA levels. Panel A (IL-4 mRNA levels at 24 hours); Panel B (IL-5 mRNA levels at 24 hours); Panel C (IL-13 mRNA levels at 24 hours); Panel D (IL-4 mRNA levels at 6 days); Panel E (IL-5 mRNA levels at 6 days); Panel F (IL-13 mRNA levels at 6 days).

Human peripheral blood was obtained by venipuncture. Peripheral blood mononuclear cells (PBMC) were isolated using Ficoll-Hypaque gradient. PBMC were stimulated in vitro with Con-A, in the presence or absence of 100 ng/ml IFN-λ1 for 24 hours or 6 days. Then, $2 \times 10^6$ PBMC were incubated in 2 ml volume in 24-well plates. Total RNA was harvested and subjected to reverse transcription. The resulting cDNA was tested for the level of expression of IL-4, IL-5 and IL-13. EF-1α was used as the reference cDNA against which the Ct for the cytokine genes was established. Samples were run in triplicate. These ΔCts are plotted in FIG. 1. Results shown non-dotted lines were the ΔCts that were higher in the presence of IFN-λ1 (indicating less cytokine signal was present). Results were compared by the Wilcoxon test for non-parametrically distributed paired data. The data show that IFN-λ1 significantly diminished the level of IL-13 mRNA at both 24 hours (12/14 donors, 0.63×[0.37-0.87] (med+semi-interquartile range) versus no IFN-λ1 (ΔΔCt method) and 6 days (12/14 donors, 0.45×[0.17-0.91] versus no IFN-λ1. While not reaching statistical significance, 8/14 donors also showed a marked decrease in IL-4 mRNA levels at 24 hours. We observed that IFN-λ2 and IFN-λ3 also possessed similar inhibitory effects on mononuclear cells as compared to that of IFN-λ1.

EXAMPLE 2

Stimulation of Peripheral Blood Mononuclear Cells Causes Specific Cytokine Release: IFN-λ Lowers Secretion of IL-4, IL-5 and IL-13, But not IFN-γ

Figure 2:
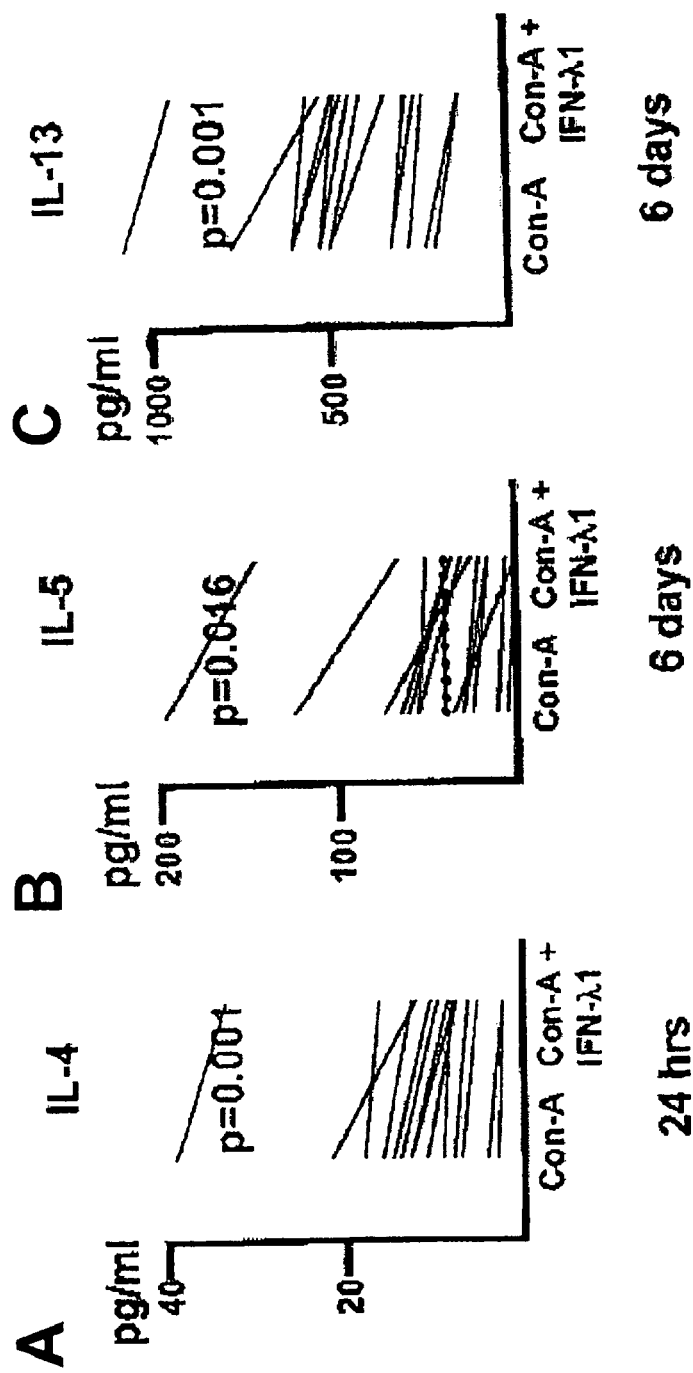
FIG. 2 shows that IFN-λ lowers secreted levels of IL-4, IL-5 and IL-13. Panel A (IL-4 levels at 24 hours); Panel B (IL-5 levels at 6 days); Panel C (IL-13 levels at 6 days).

Supernatant fluid was harvested from the cultures described in Example 1 and tested for cytokine levels by ELISA (eBiosciences). Samples were run in triplicate. IFN-λ1, was observed to reduce cytokine secretion for IL-4 at 24 hours (14/14 donors, p=0.001), and IL-5 (13/14 donors, p=0.016) and IL-13 at 6 days (14/14 donors, p=0.001). Over all 14 donors, the level of IL-4, IL-5 and IL-13 were reduced by IFN-λ by 0.33×[0.25-0.38], 0.42×[0.27-0.49] and 0.22× [0.18-0.32], respectively. IFN-γ levels were not affected by IFN-λ1. The results of the study are shown in FIG. 2.

EXAMPLE 3

IFN-λ, Reduces the Number of IL-4, -5, -13 and IFN-γ Positive Cells CD4 T-Cells

Figure 3A:
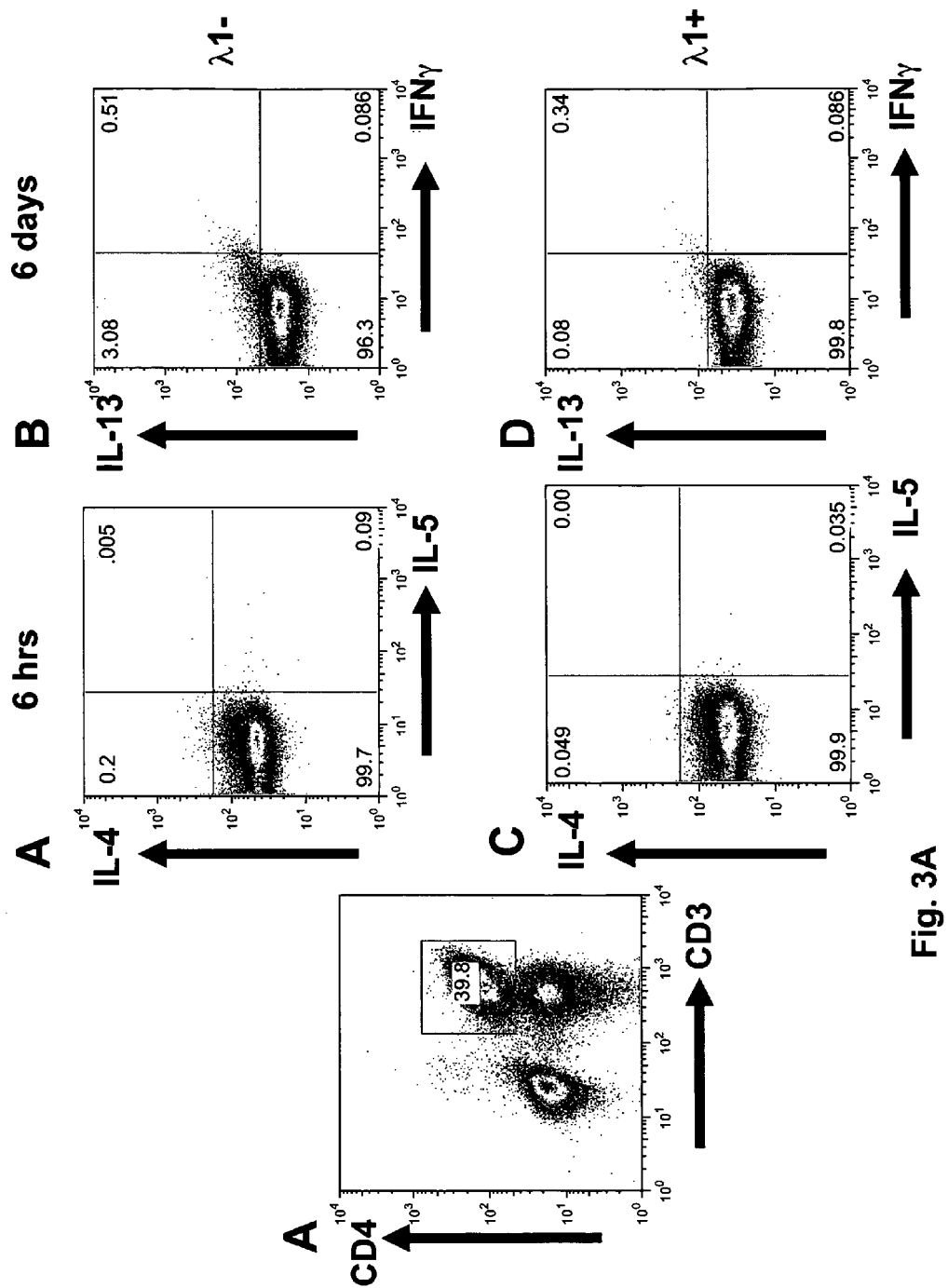
FIG. 3A shows that IFN-λ reduced the numbers of cytokine positive CD4 T-cells. Panel A, FACS analysis of CD4$^+$ and CD3$^+$ cells; Panel B, FACS analysis of IL-4$^+$ and IL-5$^+$ cells (6 hours without IFN-λ1 added); Panel C, FACS analysis of IL-13$^+$ and IFN-γ$^+$ cells (6 days without IFN-λ added); Panel D, FACS analysis of IL-4$^+$- and IL-5$^+$ cells (6 hours with IFN-λ, added); Panel E, FACS analysis of IL-13$^+$ and IFN-γ$^+$ cells (6 days with IFN-λ, added).

FACS was used to evaluate the effects of IFN-λ1 on number of IL-4, IL-5, IL-13 and IFN-γ cells. As in Example 1, cells were incubated with IFN-λ1 for 6 hours or 6 days, with no re-stimulation. Cells were gated on the CD4$^+$ population and examined by FACS for positivity with intracellular IL-4, IL-5, IL-13 and IFN-γ. Antibodies were from eBiosciences or BD BioSciences. Although the numbers of stained cells were low, IFN-λ1 reproducibly diminished the number of IL-4$^+$ CD4$^+$ T-cells (by 75%, 56% and 46%, donors A-C) at 6 hours and of IL-13$^+$ CD4 T-cells (by 84%, 54%, 48%, 75%, 49% and 42%, donors A-E (See FIG. 3)). IFN-γ$^+$ CD4$^+$ T-cells were not altered by IFN-λ1. Notwithstanding the presence of IFN-γ$^+$ T-cells and the presence of IFN-γ$^-$ in the supernatant, cells progressed through to a population of IL-13$^+$, IFN-γ$^-$ cells (See FIG. 3B). In addition, we observed that IFN-λ is effective at decreasing the number of IL-13$^+$ CD4$^+$ cells when administered 24 hours before measurement at 6 days. Thus, IFN-λ1 may be used to treat existing asthma and other Th2-associated diseases.

In sum, the present inventors have discovered an unrecognized immuno-modulatory property of IFN-λ. Our inventors found that IFN-λ is capable of down-regulating the secretion of three major Th2 and asthma-associated cytokines: namely, IL-4, IL-5 and IL-13. The effect of IFN-λ is specific, because IFN-γ secretion was not affected. IFN-λ's effect in cytokine secretion was accompanied by mRNA reduction. This was significant for IL-13 at two time points and approached significance for IL-4 at 24 hours. Not wishing to be bound by any particular theory of operability, IFN-λ is believed to act in part by reducing Th2 cytokine transcription in activated cells.

The present inventors further observed that IFN-λ decreases the number of IL-13$^+$, CD4$^+$ T-cells, as well as IL-4 positive CD4$^+$ T-cells without altering the numbers of IFN-γ cells, demonstrating a preferential, modulating effect on the Th2 system. Without wishing to be bound by any theory, IFN-λ, is proposed to diminish the secretion of IL-11, IL-13, the principle cytokine mediator of asthma and associated Th2 cytokines in healthy individuals, perhaps by a mechanism governing control of the "Th2 locus" on chromosome 5.

EXAMPLE 4

IFN-λ1 Inhibits IL-13 Production and Gives Rise to IFN-γ Production in PBMC

In Example 2, we showed that IFN-λ1 modulates IL-13 (representative of Th2 responses) with little impact on IFN-γ production (representative of Th1 responses) following mitogen (i.e., Concanavalin A) stimulation of PBMC. Here, a physiologically relevant stimulation was adopted using anti-CD2/3/28 coated MACS iBeads ("beads") to stimulate T-cells directly through their T cell receptor complex, with appropriate co-stimulation. PBMC were stimulated with beads for 3 days in the presence or absence of IFN-λ1. We observed that IFN-λ1 inhibited IL-13 production and elevated IFN-γ levels.

Figure 4:
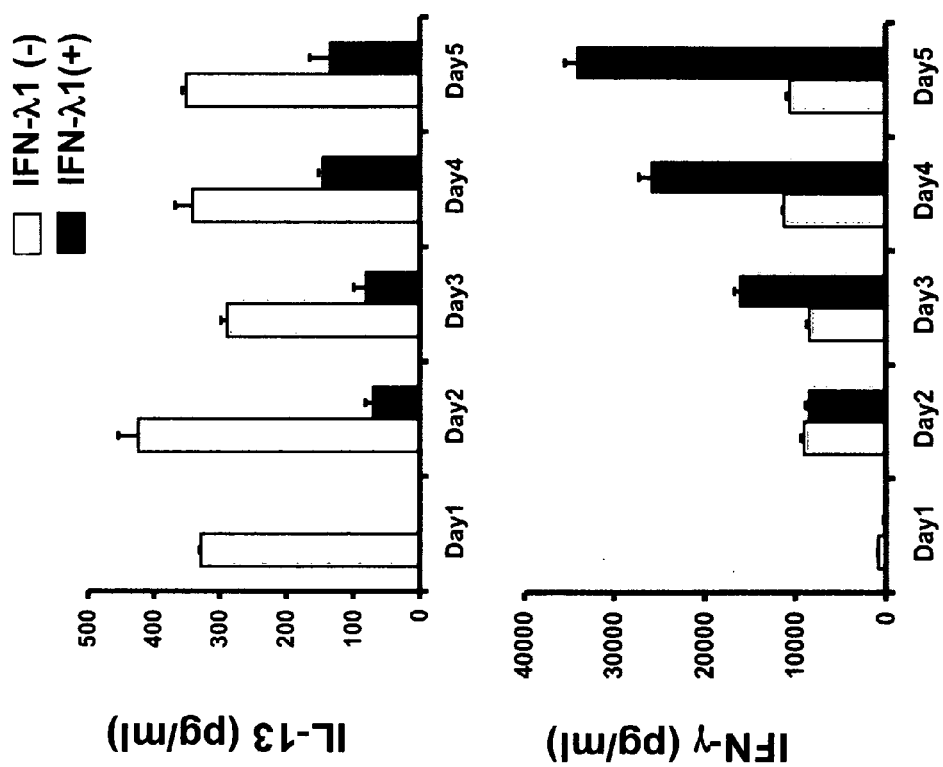
FIG. 4 shows that IFN-λ inhibited the release of IL-13. PBMC were isolated and stimulated with anti-CD2/3/28 coated beads for various days. IFN-λ completely blocked the IL-13 production at day 1, and consistently reduced IL-13 from day 2 to day 5. IFN-λ delayed the IFN-γ production.

To determine whether IL-13 production was inhibited by IFN-λ1 directly (produced early, in response to the bead stimulation), a daily time-course for this experiment was undertaken. IFN-λ1 blocked IL-13 production completely at day 1, with consistent reductions from day 2 to day 5 (56.8%-82.9% inhibition, FIG. 4). In contrast, we did not find any differences in IFN-γ production by IFN-λ1 treatment at day 1 and day 2. Thus, IFN-λ1 acted primarily to inhibit the production of IL-13. The subsequent rise in IFN-γ was therefore likely a consequence of the reduction of Th2 cytokines. Given that the stimulation used was specific for T-cells, we hypothesized that IFN-λ1 was acting directly on T-cells to inhibit IL-13 production.

EXAMPLE 5

IFN-λ1 Receptor IL-28Rα is Expressed on Both Naïve and Memory CD4$^+$ T Cells

Figure 5:
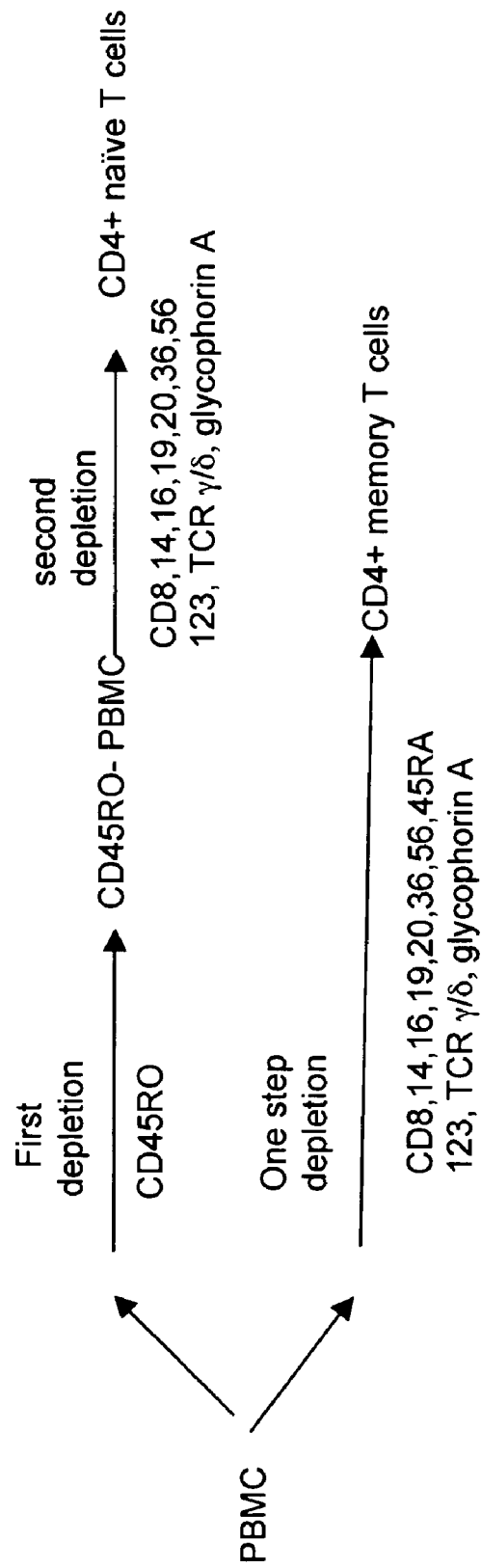
FIG. 5 shows the isolation protocol for naïve and memory T-cells from human peripheral blood using a magnetic separation kit.
Figure 6A:
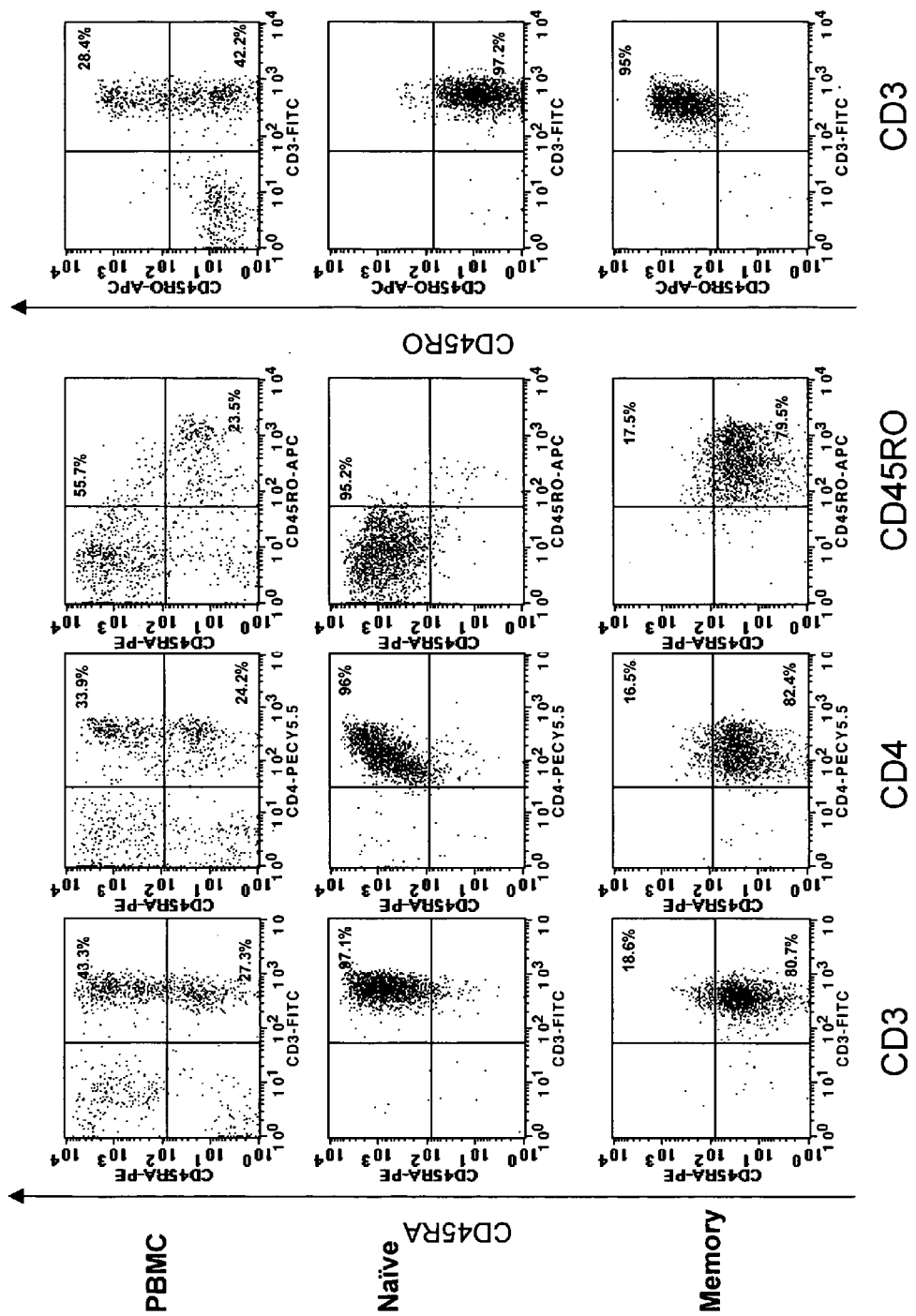
FIG. 6A shows FACS analysis of purified naïve and memory CD4$^+$ T-cells after isolation using negative isolation protocol. More than 95% of the naïve T-cells were CD3$^+$CD4$^+$CD45RA$^+$CD45RO$^-$ cells. More than 95% of the memory T-cells were CD3$^+$CD4$^+$CD45RO$^+$ cells, with a small proportion expressing both CD45RO and CD45RA.
Figure 6B:
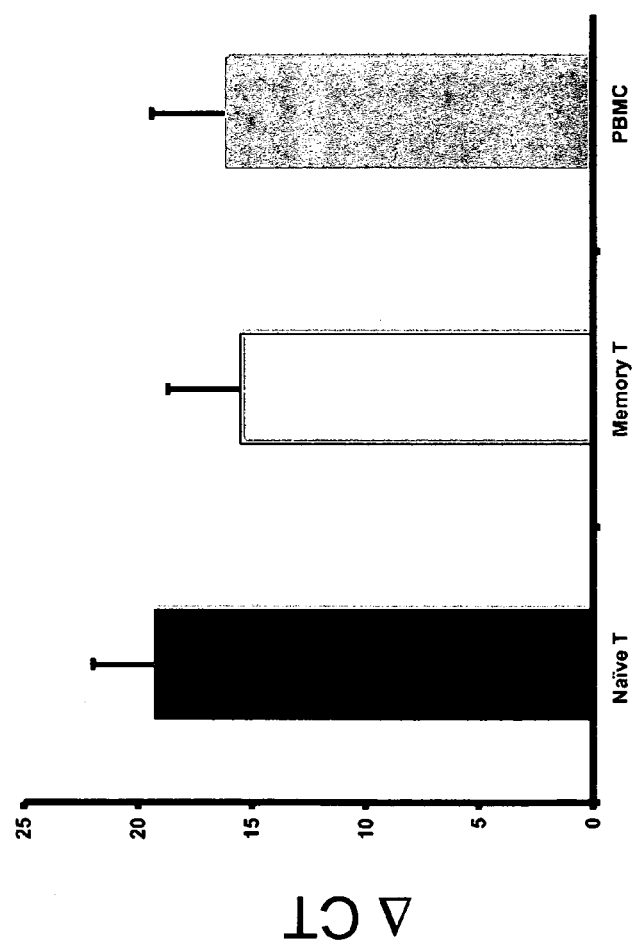
FIG. 6B shows the ΔCT of IFN-λ (IL28Rα) mRNA expression in PBMC, naïve and memory T-cells.

In order to identify IFN-λ1-responsive cell types in human PBMC, we assayed various cell types for the presence of the IFN-λ1 receptor (IL-28Rα) mRNA by qRT-PCR. "Untouched" populations of naïve and memory CD4$^+$ T-cells were purified using negative isolation (FIG. 5). More than 95% of the naïve T-cells were CD3$^+$CD4$^+$CD45RA$^+$ CD45RO$^-$ cells. Greater than 95% of the memory T-cells were CD3$^+$CD4$^+$CD45RO$^+$ cells, with a small proportion (18.6%) expressing both CD45RO and CD45RA (FIG. 6A). FIG. 6B shows the ΔCT of IL-28Rα mRNA expression in PBMC, naïve and memory T-cells. Using this approach, higher ΔCT values signify lower mRNA expression levels. The highest values were found in CD4$^+$ naïve T-cells, indicating a lower level of IL-28Rα expression on this population. Interestingly, memory CD4$^+$ T-cells expressed higher amounts of IL-28Rα mRNA levels than naïve cells, approaching that of PBMC. These data lend strong support to the hypothesis that IFN-λ1 has the ability to act directly on multiple CD4$^+$ T cell populations.

EXAMPLE 6

Figure 7A:
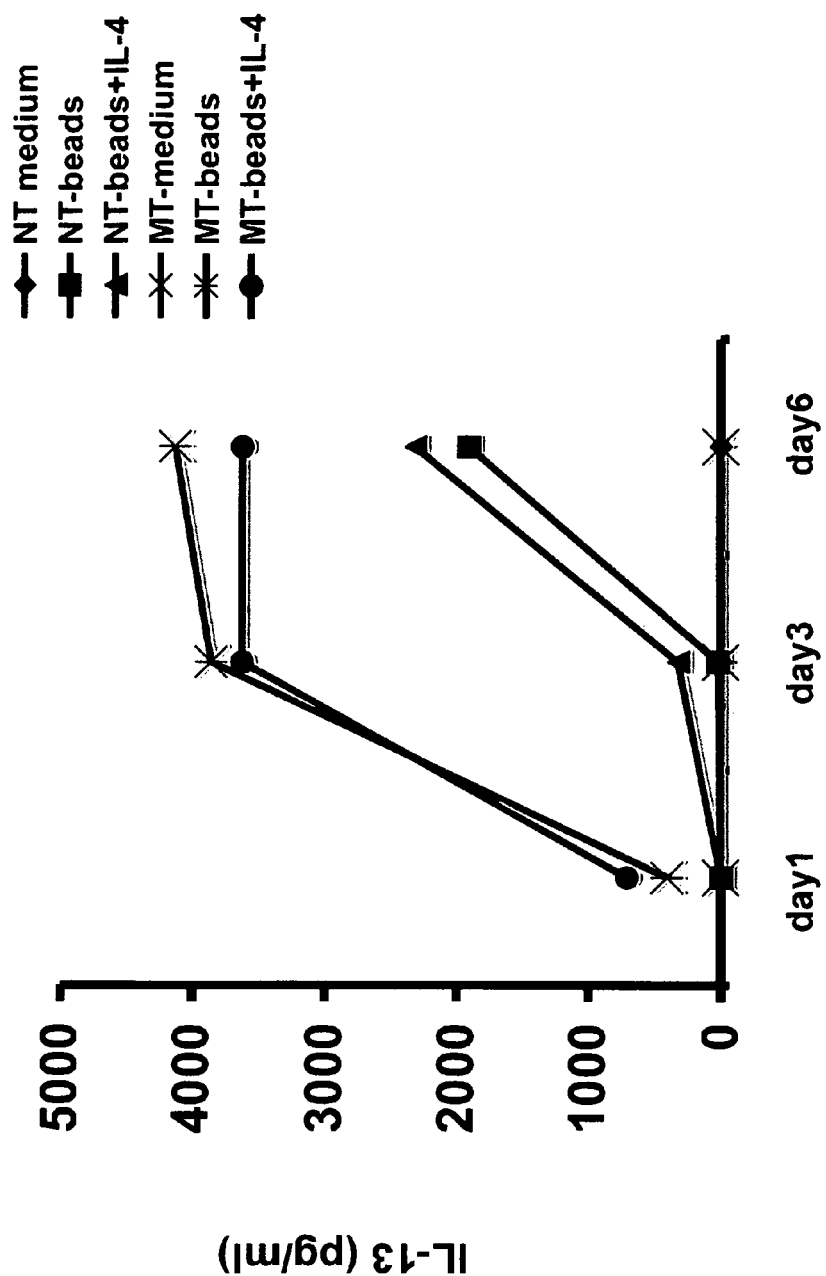
FIG. 7A shows the effect of IL-4 on naïve and memory CD4$^+$ T-cells to produce Th2 cytokine IL-13. Purified naïve and memory T-cells from the same donor were stimulated with anti-CD2/3/28 beads under neutral (beads only) or Th2 conditions (beads+IL-4).

Differential Effects of IL-4 on IL-13 Production in Naïve and Memory CD4$^+$ T-cells To determine the capacity of naïve and memory CD4$^+$ T-cells to produce the Th2 cytokine IL-13 in the presence of IL-4 (i.e., under Th2 conditions), highly purified naïve and memory T-cells from the same donor were stimulated with anti-CD2/3/28 beads under neutral (beads only) or Th2 conditions (beads+IL-4). At different time points (days 1, 3 and 6), the supernatant was collected and IL-13 production was examined by ELISA. As shown in FIG. 7A, naïve T-cells did not produce IL-13 immediately at day 1, and produced less at day 3 than memory cells were producing on day 1; as expected, memory T-cells produced a large amount of IL-13 from day 1, reaching peak levels at day 3. Interestingly, IL-4 specifically increased IL-13 production by naïve T-cells, but did not affect IL-13 production by memory T-cells at day 1 and day 3, and actually slightly inhibited their IL-13 production at day 6.

EXAMPLE 7

Figure 7B:
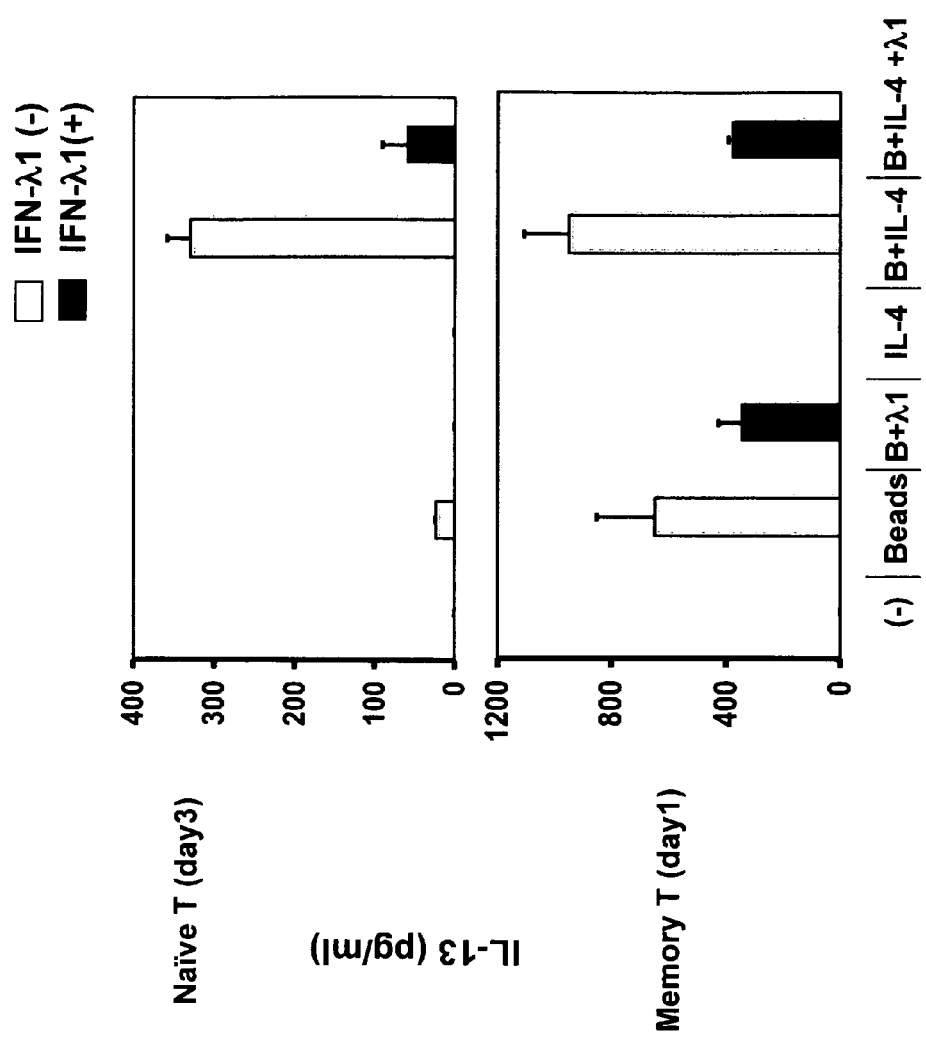
FIG. 7B shows the effect of IFN-λ in reducing IL-13 production in both naïve and memory T-cells.
Figure 7C:
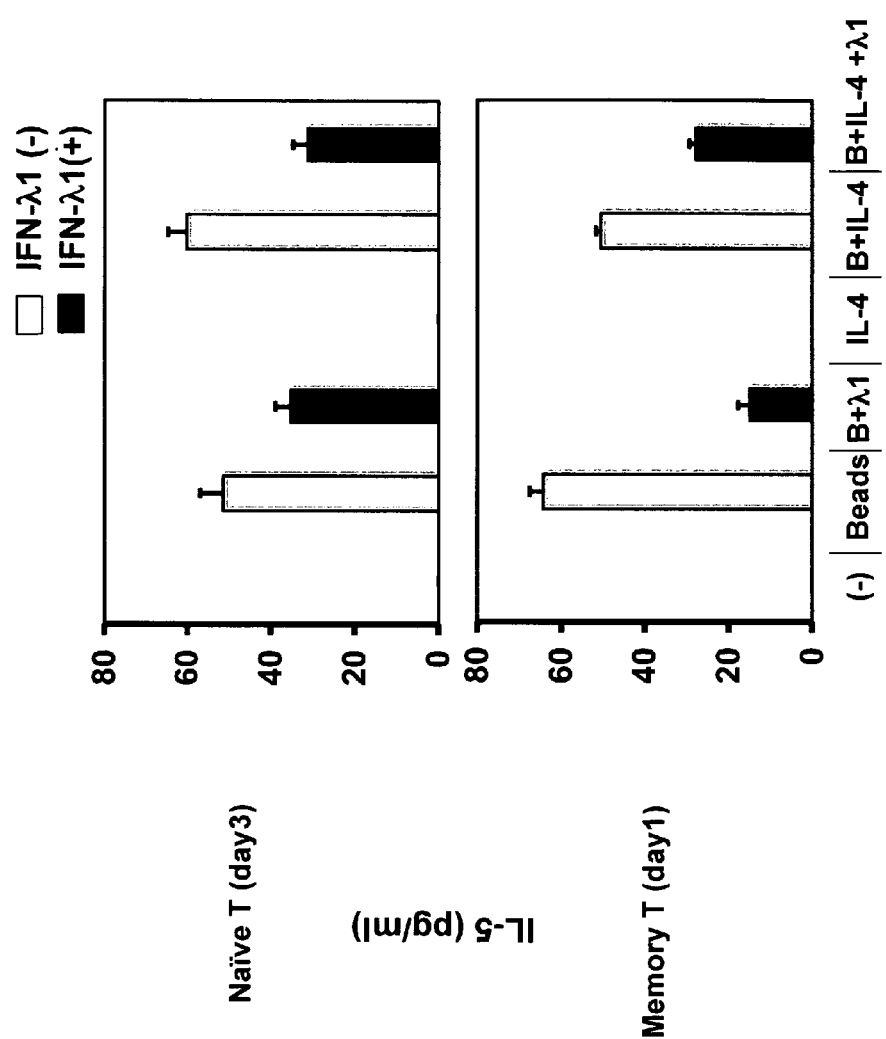
FIG. 7C shows the effect of IFN-λ in reducing IL-5 production in both naïve and memory T-cells.

IFN-λ1 Directly Inhibits Th2 Cytokine Production by Either Naïve or Memory T-Cells Given that both naïve and memory cells expressed IL-28Rα (FIG. 6B), we next characterized the direct effect of IFN-λ1 on Th2 cytokine production. In the absence of other cell types, purified naïve or memory CD4$^+$ T-cells were stimulated under neutral (beads alone) or Th2 conditions (beads+IL-4), in the presence or absence of IFN-λ1. Supernatants were assayed by ELISA for the Th2 cytokines IL-13 and IL-5. As shown in FIGS. 7B and 7C, naïve CD4$^+$ T-cells did not produce any Th2 cytokines at day 1 (data not shown); only after the cells were driven towards a Th2 phenotype did they produce IL-13 and IL-5 (day 3 or day 6). Likewise, IL-4 significantly enhanced IL-13 production by naïve T-cells. Notably, this increased IL-13 production was greatly reduced by IFN-λ1, suggesting it may act specifically to antagonize the activity of IL-4. In contrast, under the same Th2 polarizing conditions, IL-13 and IL-5 production were induced in memory T-cells immediately after overnight stimulation. Interestingly, IFN-λ1 immediately inhibited their IL-13 and IL-5 production under both neutral and Th2 conditions. Similar inhibitions were seen at day 3, and less of an effect was observed at day 6, (data not shown).

In sum, IL-13 and IL-5 secretion was inhibited by IFN-λ under neutral and Th2 conditions, in naïve and memory CD4$^+$ T-cells. This occurred independently of a rise in Th1-associated cytokines, and was also observed in the presence of neutralizing antibody to IFN-γ.

EXAMPLE 8

Figure 8A:
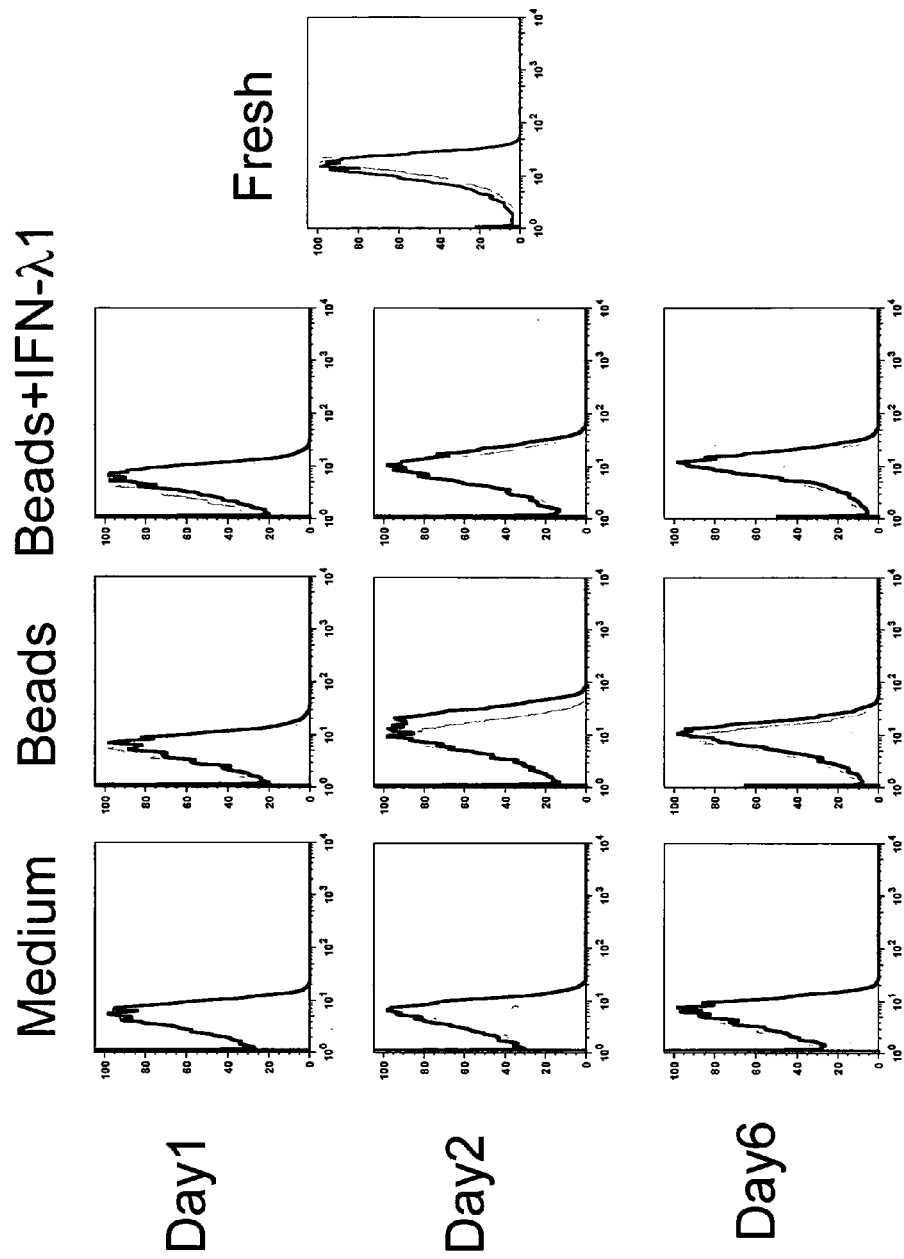
FIG. 8A shows expression of IL-4Rα on freshly isolated naïve CD4$^+$ T-cells following stimulation with anti-CD2/3/28 beads.
Figure 8B:
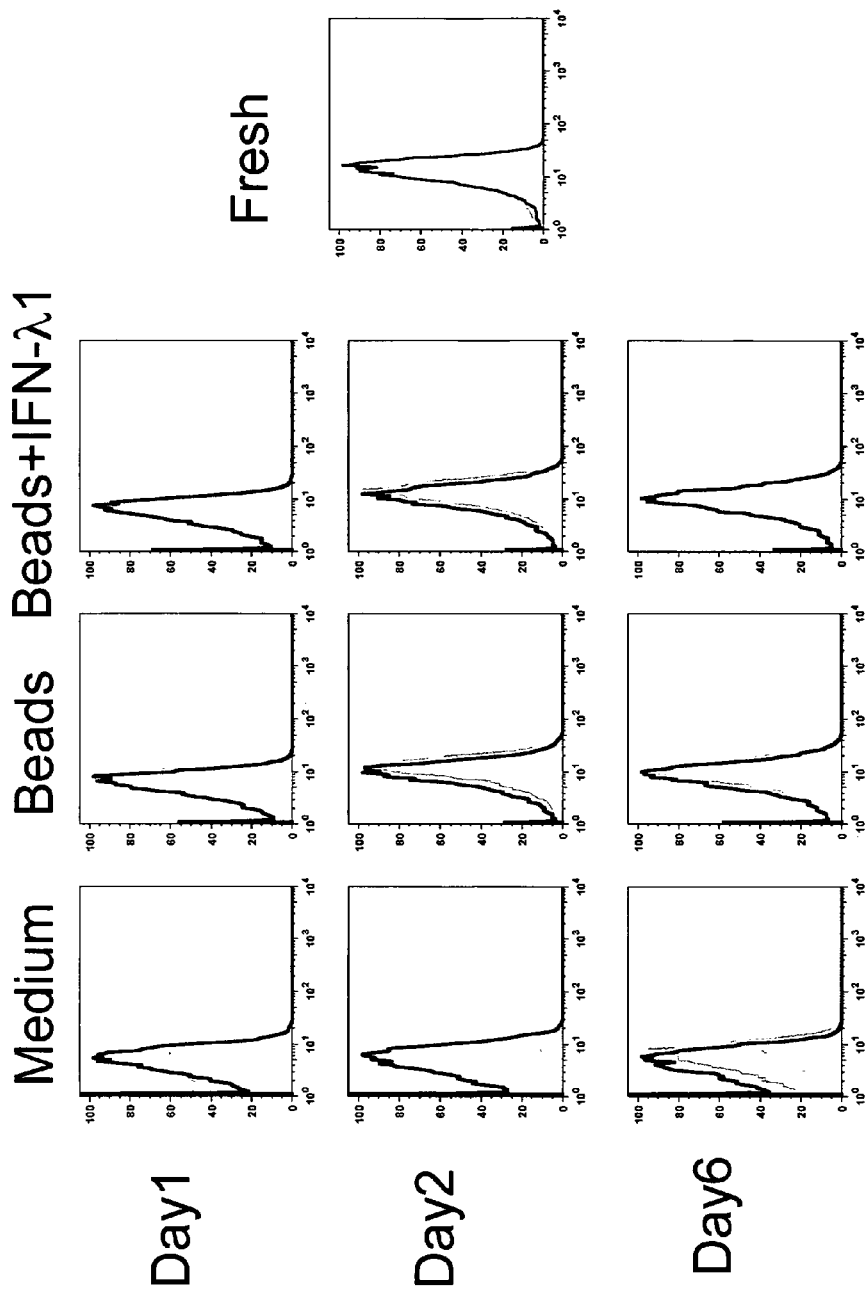

Differential Expression of IL-4Rα on Naïve and Memory T-Cells and the Effect of IFN-λ1 on IL-4Rα Expression To determine whether IFN-λ1 specifically antagonized the activity of IL-4 on naïve T-cells through the regulation of the IL-4 signaling pathway, IL-4Rα expression on naïve and memory T-cells was measured by flow cytometry, with or without stimulation, in the presence or absence of IFN-λ1 at different time points. As shown in FIGS. 8A and 8B, freshly isolated naïve and memory CD4$^+$ T-cells did not express IL-4Rα on their surface. However, IL-4Rα expression was detected after 48 hr stimulation with anti-CD2/3/28 beads, but only on naïve T-cells. Remarkably, naïve T-cells that were stimulated in the presence of IFN-λ1 did not express detectable cell-surface expression levels of IL-4Rα, suggesting that IFN-λ1 down-regulated, or prevented, the expression of IL-4Rα. In contrast, IL-4Rα expression was not detectable on memory T-cells with or without stimulation, in any culture conditions through the whole culture period (6 days), which is consistent with our observation that IL-4 was not required for IL-13 production by memory CD4$^+$ T-cells.

EXAMPLE 9

IFN-λ1 Regulates Expression of GATA3 and T-Bet

We next addressed whether downstream signaling can be modulated by IFN-λ1. As widely recognized, the polarized cytokine profiles of Th1 and Th2 cells are primarily dictated by the mutually exclusive expression of the "master" Th1 and Th2 transcription factors, T-bet and GATA3. IL-4 stimulation through the IL-4R leads to phosphorylation of STAT6 and upregulation of GATA3 expression, while IL-12 and IFN-γ perform the complementary function of upregulating T-bet.

Figure 9:
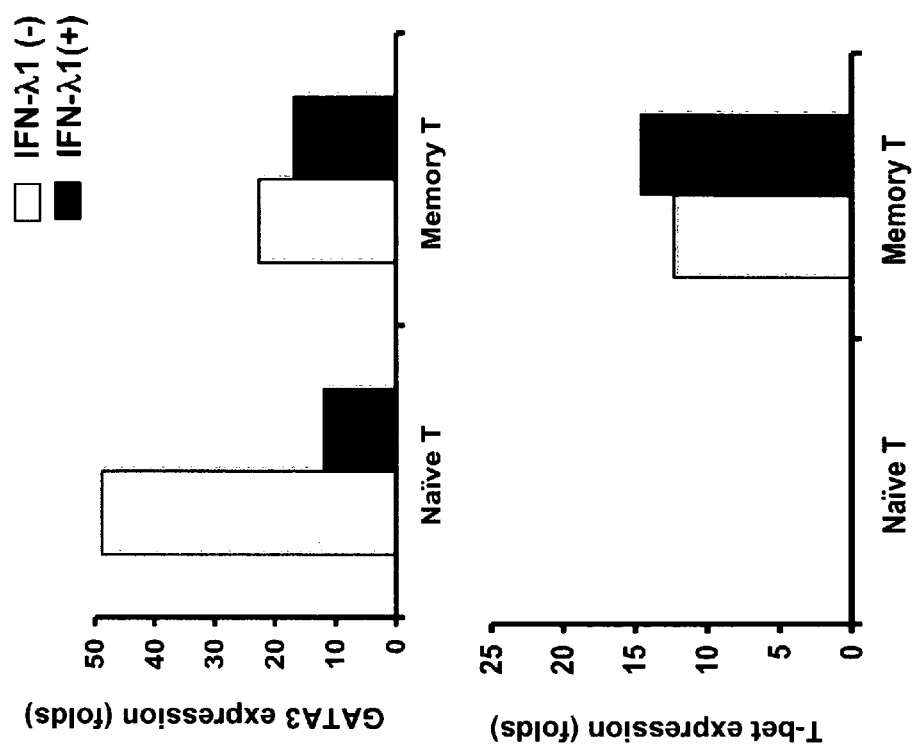
FIG. 9 shows GATA3 and T-bet expression in purified naïve and memory CD4$^+$ T-cells following Th2 conditions (i.e., beads+IL-4) for 18 hours. IFN-λ1 inhibited the expression of GATA3 expression (as measured by qRT-PCR) 4-fold in naïve T-cells. Memory T-cells exhibited only small changes in either GATA3 or T-bet expression.

In these experiments, purified naïve or memory CD4$^+$ T-cells were stimulated under Th2-polarizing conditions (beads+IL-4) for 18 hr, in the presence or absence of IFN-λ1. RNA was harvested for qRT-PCR quantitation of T-bet and GATA3 expression. As shown in FIG. 9, expression of GATA3 by naïve T-cells was decreased 4-fold (3-6 fold, depending on the donor) upon treatment with IFN-λ1. As expected, T-bet expression was barely detectable under Th2 conditions. Memory T-cells on the other hand, exhibited only small changes in either GATA3 or T-bet expression. Considering the heterogeneous composition of memory CD4$^+$ T-cells, it is possible that the presence of non-Th2 polarized or non-Th1 polarized has diminished our ability to measure any changes in GATA3 or T-bet expression. Nonetheless, these data strongly support the direct inhibition of Th2 polarization by IFN-λ1, through the regulation of the Th2-restricted transcription factor GATA3, and that this effect is most pronounced in naïve CD4$^+$ T-cells.

EXAMPLE 10

IFN-λ1 Does not Modulate the Proliferation of Naïve CD4$^+$ T-Cells

Figure 10:
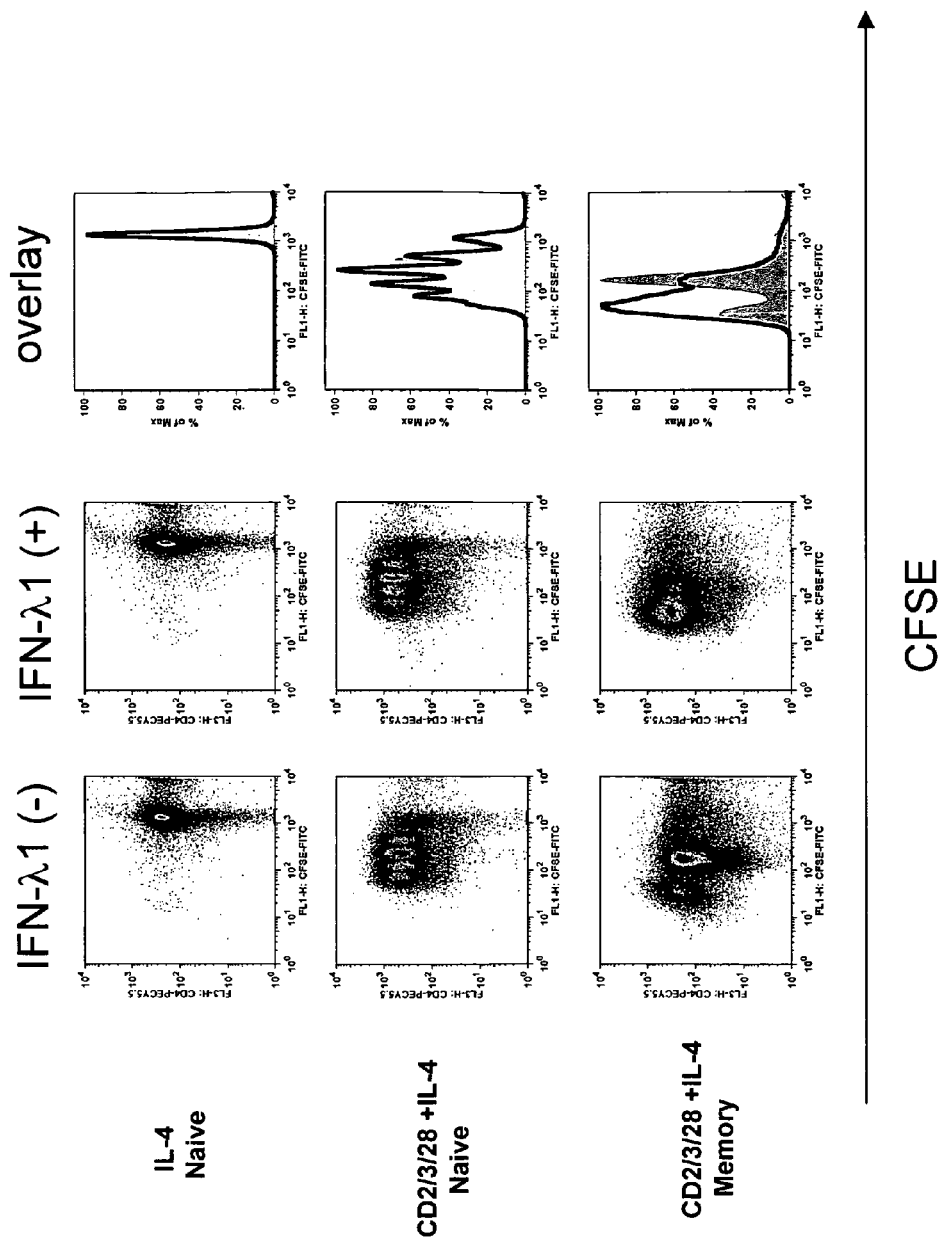
FIG. 10 shows the effect of IFN-λ1 on CD4$^+$ T cell proliferation of naïve and memory T-cells using a CFSE dilution method. Naïve T-cells proliferated more extensively than memory T-cells under Th2 conditions. IFN-λ did not affect proliferation of naïve CD4$^+$ T-cells.

To characterize the potential effects of IFN-λ1 on T cell function, and to determine whether the decrease in cytokine production was due to inhibition of T cell proliferation, we assessed its effect on T cell proliferation. Using the CFSE dilution method, we defined the effect of IFN-λ1 on CD4$^+$ T cell proliferation in naïve and memory cells. In these experiments, IL-4 alone did not induce proliferation of naïve or memory T-cells. As shown in FIG. 10, naïve T-cells proliferated more extensively than memory T-cells under Th2 conditions. IFN-λ1 did not affect proliferation of naïve CD4$^+$ T-cells, which undertook four rounds of division over the 6-day culture period. A minor enhancement of proliferation was noted in memory cells. No significance difference in the morphology of expanded naïve T-cells or memory T-cells was observed in the presence or absence of IFN-λ1.

EXAMPLE 11

IFN-λ1 Inhibits T Cell Differentiation

We investigated whether IFN-λ1 affects the phenotype or differentiation of naïve and memory T-cells upon activation. Two memory T cell subsets have previously been defined based on their expression of the lymph node homing receptors CD62L and CCR7 and designated "central memory"-like T-cells (CD62L$^+$CCR7$^+$; which primarily reside in lymphoid tissue), and "effector memory" T-cells (CD62L$^-$CCR7$^-$; which are the predominant subset in non-lymphoid tissue, including the periphery). We examined the expression of these two homing receptors on rive and memory CD4$^+$ T-cells after stimulation under either neutral or Th2 conditions, in the presence or absence of IFN-λ1.

Figure 11A:
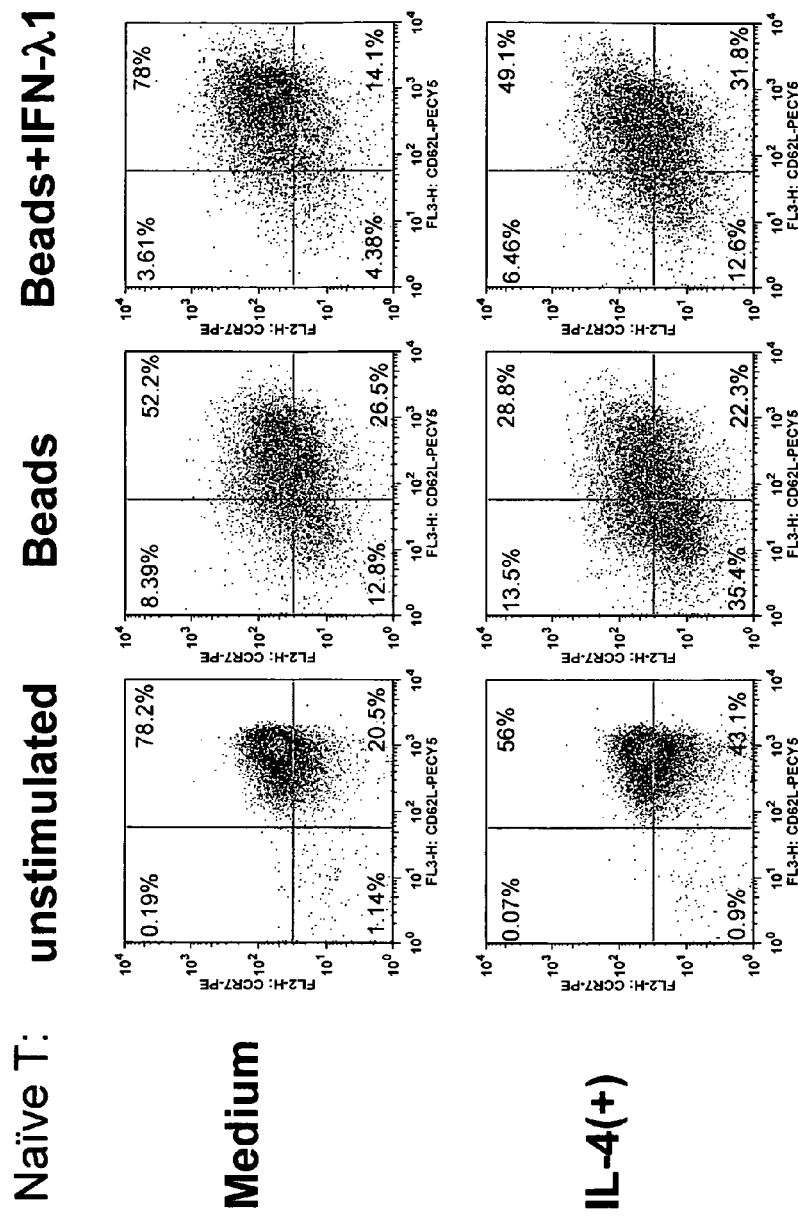
FIG. 11A shows that IFN-λ prevented the activation-induced down-regulation of CD62L under both neutral and Th2 conditions on naïve CD4$^+$ T-cells. Bead activation induced the differentiation of CD62L$^+$CCR7$^+$ cells into CD62L$^-$CCR7$^-$ cells. IFN-λ significantly prevented the activation-induced differentiation of naïve cells and maintained the phenotype of CD62L$^+$CCR7$^+$.
Figure 11B:
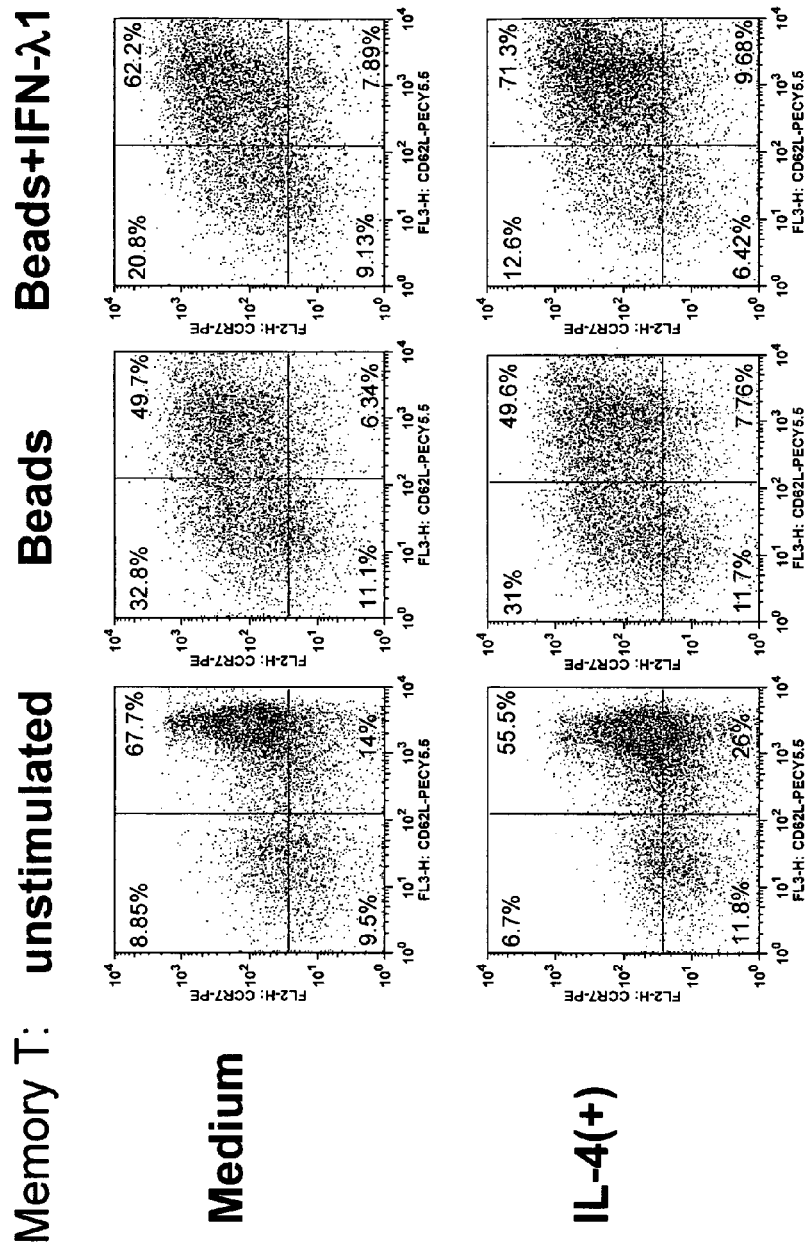

As shown in FIGS. 11A and 11B, IFN-λ1 prevented the activation-induced down-regulation of CD62L under both neutral and Th2 conditions, on both naïve or memory CD4⁺ T-cells. Freshly-isolated naïve CD4⁺ T-cells were CD62L⁺CCR7⁺. After the 3-day culture period, the majority of un-stimulated, (previously naïve) cells had retailed this "central memory-like" phenotype and were CD62L⁺CCR7⁺ (78.2%). When exposed only to IL-4 for 3 days, a smaller proportion of these cells was CD62L⁺CCR7⁺(56%). Bead-mediated activation caused a loss of this double positive population, both in medium alone (78.2% to 52.2%) and in the presence of IL-4 (56% to 28.8%). The decrease coincided with an increase in cells with a CD62L⁻CCR7⁻ phenotype (12.8% and 35.4%, respectively). Therefore, bead activation induced the differentiation of CD62L⁺CCR7⁺ cells into CD62L⁻CCR7⁻, effector-memory-like cells; this process was enhanced by IL-4. The presence of IFN-λ1 in the medium significantly prevented this activation-induced differentiation of naïve T-cells and maintained the phenotype of CD62L⁺CCR7⁺ in activated naïve T-cells, in the presence or absence of IL-4 (49.2% and 78%, respectively).

The majority of memory CD4⁺ T-cells was central memory-like T-cells, whether they were cultured with medium alone (67.7%) or in the presence of IL-4 (55.5%). Upon stimulation with beads, these cells continued to express CCR7, but down-regulated CD62L (un-stimulated vs. bead-stimulated cells: 8.85% vs 32.8% CD62L–CCR7+), with a corresponding reduced percentage of central memory-like T-cells (49%). IL-4 did not alter the differentiation of memory T-cells upon activation with beads. However, IFN-λ1 once again inhibited the differentiation of these central memory-like T-cells into CD62L⁻CCR7⁺ cells, and maintained their double positive phenotype of non-activated central memory-like cells (62.2%). Thus, IFN-λ1 prevented the activation-induced differentiation of central memory T-cells, and may represent a mechanism by which effector cells are sequestered in the lymph node and rendered incapable of entry into the periphery by modulation of their homing receptor expression.

EXAMPLE 12

Human PBMC were isolated from human blood as described above in Example 1. PBMC were pre-treated with IFN-λ1 (100 ng/ml) for various time periods (i.e., 1, 2, 4 or 8 hours). After IFN-λ1 pretreatment, mononuclear cells were washed free of all added IFN-λ1. Washed cells were then stimulated with CD2/3/28 coated beads, as described. After three days of stimulation, culture supernatants were harvested and the level of secreted IL-13 was quantified by ELISA. As shown in FIG. 12, pre-treatment of mononuclear cells with IFN-λ1 for a time period of 2 hours or less produced a marginal decreased in IL-13 secretion. Pre-treatment of mononuclear cells with IFN-λ1 for a time period of 4 hours or greater produced a down-regulation of IL-13 secretion. Overall, we observed that IFN-λ pre-treatment of mononuclear cells is generally mimicking that of IFN-λ co-incubation with mononuclear cells, in terms of the inhibitory effects on Th2 cytokines.

The Examples are merely illustrative of the invention and are not intended to limit the scope of the invention. One of skill in the art will recognize that various modifications may be made to the embodiments described herein without departing from the spirit and scope of the invention, which is defined by the appended claims.

---

What is claimed is:

1. A method of ex vivo treatment of mononuclear cells, comprising the steps of:
    (a) obtaining peripheral blood from a human subject;
    (b) isolating mononuclear cells from said peripheral blood;
    (c) exposing said isolated mononuclear cells to interferon lambda (IFN-λ); and
    (d) administering said exposed cells to said human subject, wherein said IFN-λ is present in an amount sufficient to inhibit a stimulus-induced cytokine release, and wherein said stimulus is selected from the group consisting of Concanavalin A and anti-CD2/3/28 beads and said cytokine is at least one compound selected from the group consisting of interleukin-4 (IL-4) and interleukin-5 (IL-5).

2. The method of claim 1, wherein said IFN-λ is at least one compound selected from the group consisting of IFN-λ1, IFN-λ2, and IFN-λ3.

3. The method of claim 1, wherein said IFN-λ amount is the range about 1 ng/mL to about 200 μg/mL.

4. The method of claim 1, wherein said IFN-λ amount is in the range of about 100 ng/mL to about 10 μg/mL.

5. The method of claim 1, wherein said exposing step is performed for about 1 hour to about 24 hours.

6. The method of claim 1, wherein said exposing step is performed for about 6 hours to about 12 hours.

7. The method of claim 1, wherein said human subject is suffering form asthma.

8. The method of claim 7, wherein said asthma is virus-induced or allergen-induced.

9. The method of claim 1, wherein said mononuclear cells are the range of about $1 \times 10^7$ cells to about $1 \times 10^9$ cells.

10. The method of claim 1, wherein said mononuclear cells are about $1 \times 10^8$ cells.

11. The method of claim 1, further comprising the step of repeating the step (a) through step (d).

12. The method of claim 1, further comprising the step (e) of administering a composition comprising IFN-λ to the human subject.

13. The method of claim 12, wherein said IFN-λ composition is administered nasally, intravenously, or orally.

14. The method of claim 12, wherein said step (e) is performed simultaneously or sequentially with step (d).

* * * * *

SEQUENCE LISTING

```
<160> NUMBER OF SEQ ID NOS: 11

<210> SEQ ID NO 1
<211> LENGTH: 200
<212> TYPE: PRT
<213> ORGANISM: Homo sapiens
<300> PUBLICATION INFORMATION:
<308> DATABASE ACCESSION NUMBER: GenBank Accession No: Q8IU54

<400> SEQUENCE: 1

Met Ala Ala Ala Trp Thr Val Val Leu Val Thr Leu Val Leu Gly Leu
1               5                   10                  15

Ala Val Ala Gly Pro Val Pro Thr Ser Lys Pro Thr Thr Thr Gly Lys
            20                  25                  30

Gly Cys His Ile Gly Arg Phe Lys Ser Leu Ser Pro Gln Glu Leu Ala
        35                  40                  45

Ser Phe Lys Lys Ala Arg Asp Ala Leu Glu Glu Ser Leu Lys Leu Lys
    50                  55                  60

Asn Trp Ser Cys Ser Ser Pro Val Phe Pro Gly Asn Trp Asp Leu Arg
65                  70                  75                  80

Leu Leu Gln Val Arg Glu Arg Pro Val Ala Leu Glu Ala Glu Leu Ala
                85                  90                  95

Leu Thr Leu Lys Val Leu Glu Ala Ala Ala Gly Pro Ala Leu Glu Asp
            100                 105                 110

Val Leu Asp Gln Pro Leu His Thr Leu His His Ile Leu Ser Gln Leu
            115                 120                 125
```

Gln Ala Cys Ile Gln Pro Gln Pro Thr Ala Gly Pro Arg Arg Gly
    130                 135                 140

Arg Leu His His Trp Leu His Arg Leu Gln Glu Ala Pro Lys Lys Glu
145                 150                 155                 160

Ser Ala Gly Cys Leu Glu Ala Ser Val Thr Phe Asn Leu Phe Arg Leu
                165                 170                 175

Leu Thr Arg Asp Leu Lys Tyr Val Ala Asp Gly Asn Leu Cys Leu Arg
            180                 185                 190

Thr Ser Thr His Pro Glu Ser Thr
        195                 200

<210> SEQ ID NO 2
<211> LENGTH: 200
<212> TYPE: PRT
<213> ORGANISM: Homo sapiens
<300> PUBLICATION INFORMATION:
<308> DATABASE ACCESSION NUMBER: GenBank Accession No: Q8IZJ0

<400> SEQUENCE: 2

Met Lys Leu Asp Met Thr Gly Asp Cys Thr Pro Val Leu Val Leu Met
1               5                   10                  15

Ala Ala Val Leu Thr Val Thr Gly Ala Val Pro Val Ala Arg Leu His
                20                  25                  30

Gly Ala Leu Pro Asp Ala Arg Gly Cys His Ile Ala Gln Phe Lys Ser
            35                  40                  45

Leu Ser Pro Gln Glu Leu Gln Ala Phe Lys Arg Ala Lys Asp Ala Leu
        50                  55                  60

Glu Glu Ser Leu Leu Lys Asp Cys Arg Cys His Ser Arg Leu Phe
65                  70                  75                  80

Pro Arg Thr Trp Asp Leu Arg Gln Leu Gln Val Arg Glu Arg Pro Met
                85                  90                  95

Ala Leu Glu Ala Glu Leu Ala Leu Thr Leu Lys Val Leu Glu Ala Thr
            100                 105                 110

Ala Asp Thr Asp Pro Ala Leu Val Asp Val Leu Asp Gln Pro Leu His
        115                 120                 125

Thr Leu His His Ile Leu Ser Gln Phe Arg Ala Cys Ile Gln Pro Gln
    130                 135                 140

Pro Thr Ala Gly Pro Arg Thr Arg Gly Arg Leu His His Trp Leu Tyr
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200

<210> SEQ ID NO 3
<211> LENGTH: 200
<212> TYPE: PRT
<213> ORGANISM: Homo sapiens
<300> PUBLICATION INFORMATION:
<308> DATABASE ACCESSION NUMBER: GenBank Accession No: Q8IZI9

<400> SEQUENCE: 3

Met Lys Leu Asp Met Thr Gly Asp Cys Met Pro Val Leu Val Leu Met
1               5                   10                  15

Ala Ala Val Leu Thr Val Thr Gly Ala Val Pro Val Ala Arg Leu Arg
                20                  25                  30

-continued

Gly Ala Leu Pro Asp Ala Arg Gly Cys His Ile Ala Gln Phe Lys Ser
         35                  40                  45

Leu Ser Pro Gln Glu Leu Gln Ala Phe Lys Arg Ala Lys Asp Ala Leu
 50                  55                  60

Glu Glu Ser Leu Leu Leu Lys Asp Cys Lys Cys Arg Ser Arg Leu Phe
65                  70                  75                  80

Pro Arg Thr Trp Asp Leu Arg Gln Leu Gln Val Arg Glu Arg Pro Val
             85                  90                  95

Ala Leu Glu Ala Glu Leu Ala Leu Thr Leu Lys Val Leu Glu Ala Thr
        100                 105                 110

Ala Asp Thr Asp Pro Ala Leu Gly Asp Val Leu Asp Gln Pro Leu His
        115                 120                 125

Thr Leu His His Ile Leu Ser Gln Leu Arg Ala Cys Ile Gln Pro Gln
    130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
            195                 200

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ccagccagtc cagatcactc t                                          21

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
acagcagtat cagaagcgat gg                                         22

<210> SEQ ID NO 6
<211> LENGTH: 16
<212> TYPE: DNA
<213> ORGANISM: Artificial
<220> FEATURE:
<223> OTHER INFORMATION: Primer

<400> SEQUENCE: 6
accacctgtt gtggtc                                                16

<210> SEQ ID NO 7
<211> LENGTH: 16
<212> TYPE: DNA
<213> ORGANISM: Artificial
<220> FEATURE:
<223> OTHER INFORMATION: Primer

<400> SEQUENCE: 7

-continued

```
cctttccaca ctgcac                                                    16

<210> SEQ ID NO 8
<211> LENGTH: 16
<212> TYPE: DNA
<213> ORGANISM: Artificial
<220> FEATURE:
<223> OTHER INFORMATION: Primer

<400> SEQUENCE: 8
tcaaggcaac cacgtc                                                    16

<210> SEQ ID NO 9
<211> LENGTH: 16
<212> TYPE: DNA
<213> ORGANISM: Artificial
<220> FEATURE:
<223> OTHER INFORMATION: Primer

<400> SEQUENCE: 9
gatggacgtc ttggag                                                    16

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ctgaaccatc caggccaaat                                                20

<210> SEQ ID NO 11
<211> LENGTH: 18
<212> TYPE: DNA
<213> ORGANISM: Artificial
<220> FEATURE:
<223> OTHER INFORMATION: Primer

<400> SEQUENCE: 11
gccgtgtggc aatccaat                                                  18
```